United States Patent [19]

Narr et al.

[11] Patent Number: 4,831,027
[45] Date of Patent: May 16, 1989

[54] IMIDAZO-BENZOXAZINONES, THE PREPARATION THEREOF AND PHARMACEUTICAL COMPOSITIONS CONTAINING THESE COMPOUNDS

[75] Inventors: Berthold Narr; Norbert Hauel, both of Biberach; Klaus Noll; Joachim Heider, both of Warthausen; Manfred Psiorz; Andreas Bomhard, both of Biberach; Jacques van Meel; Willi Diederen, both of Biberach, all of Fed. Rep. of Germany

[73] Assignee: Dr. Karl Thomae GmbH, Biberach an der Riss, Fed. Rep. of Germany

[21] Appl. No.: 105,144

[22] Filed: Oct. 5, 1987

[30] Foreign Application Priority Data

Oct. 4, 1986 [DE] Fed. Rep. of Germany ....... 3633861

[51] Int. Cl.$^4$ ............... A61K 31/535; C07D 498/04
[52] U.S. Cl. ..................... 514/212; 514/218; 514/229.8; 540/492; 540/575; 540/599; 544/73; 544/95
[58] Field of Search ........... 544/73, 95; 540/492, 540/575, 599; 514/212, 218, 228, 231, 232, 234, 237, 239, 229.8

[56] References Cited

U.S. PATENT DOCUMENTS 3,883,521  5/1975  Fauran et al. .................... 544/95

FOREIGN PATENT DOCUMENTS 2227489  12/1972  Fed. Rep. of Germany .
2349480   4/1975  Fed. Rep. of Germany .

OTHER PUBLICATIONS

Stevenson et al., J. Org. Chem., vol. 51 (1988), pp. 616–620.
Leonard et al., Chemical Abstracts, vol. 107 (1987), 77749m.
Leonard et al., J. Org. Chem., vol. 52 (13), (1987), pp. 2933–2935.

Primary Examiner—Richard L. Raymond
Attorney, Agent, or Firm—D. E. Frankhouser; Mary-Ellen M. Timbers; Alan R. Stempel

[57] ABSTRACT

The invention relates to new imidazo-benzoxazinones of formula

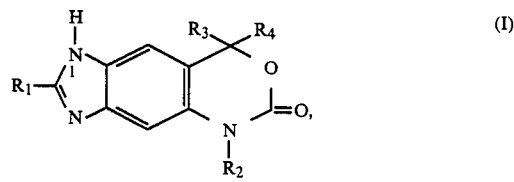

wherein the substituents are defined herein below, which compounds are useful in the treatment of cardiovascular disorders.

10 Claims, No Drawings

IMIDAZO-BENZOXAZINONES, THE PREPARATION THEREOF AND PHARMACEUTICAL COMPOSITIONS CONTAINING THESE COMPOUNDS

The present invention relates to new imidazo-benzoxazinones of formula

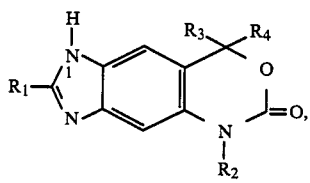 (I)

the 3H-tautomers and acid addition salts thereof, particularly, for pharmaceutical use, the physiologically acceptable acid addition salts thereof with organic or inorganic acids, which have valuable pharmacological properties, particularly antithrombotic and cardiovascular properties, as well as pharmaceutical compositions containing these compounds and processes for preparing them.

In formula I above $R_1$ represents an alkyl group optionally substituted by a phenyl or pyridyl group, an alkyl group with 4 to 6 carbon atoms, a mercapto group optionally substituted by an alkyl group, a vinyl group which is substituted in the end position by a phenyl or pyridyl group, a phenyl group optionally substituted by a halogen atom or by a hydroxy, alkoxy, mercapto, alkylmercapto, alkylsulphinyl, alkylsulphonyl, cyano, amino or nitro group (whilst a hydroxyphenyl group may additionally be substituted by one or two alkyl groups each having 1 to 4 carbon atoms or an aminophenyl group may be substituted by one or two halogen atoms), a phenyl group disubstituted by halogen atoms, hydroxy, alkoxy, mercapto, alkylmercapto, alkylsulfinyl or alkylsulfonyl groups, the substituents of the phenyl nucleus being either identical or different, a 5- or 6-membered heteroaromatic ring bound via a carbon atom and containing an oxygen, sulphur or nitrogen atom, two or three nitrogen atoms or one nitrogen atom and one oxygen or sulphur atom, to which one or two 1,4-butadienyl groups may additionally be bonded via two adjacent carbon atoms, whilst in the case of the pyridines these may additionally be substituted by an amino, alkanoylamino or morpholino group or by two halogen atoms or by one halogen atom and an amino or morpholino group, or $R_1$ represents a 5- to 7-membered saturated imino-, N-alkyl-imino- or N-alkanoyl-imino-alkylene ring, bonded via a carbon atom, in which a methylene group in the 4-position may be replaced by an imino, alkylimino or alkanoylimino group or a —$CH_2CH_2$ group may be replaced by an —NH—CO— group, whilst the CO group of this —NH—CO— group must be linked to the existing N atom, and moreover all the above-mentioned heteroaromatic rings and saturated rings may be substituted by an alkyl group, $R_2$ represents a hydrogen atom, an alkyl group with 1 to 6 carbon atoms optionally substituted from position 2 by a hydroxy or alkoxy group, or a phenylalkyl group, $R_3$ and $R_4$, which may be identical or different, represent hydrogen atoms or alkyl groups, whilst the alkyl moiety of all the above-mentioned groups may contain from 1 to 3 carbon atoms unless otherwise stated.

As examples of the definitions of group $R_1$ to $R_4$ given hereinbefore:

$R_1$ may represent a methyl, ethyl, n-propyl, isopropyl, n-butyl, isobutyl, tert.butyl, n-pentyl, 1-methyl-n-butyl, 2-methyl-n-butyl, 3-methyl-n-butyl, 1-ethyl-n-propyl, tert.pentyl, n-hexyl, benzyl, 1-phenylethyl, 2-phenylethyl, 3-phenylpropyl, pyridylmethyl, 1-pyridylethyl, 2-pyridylethyl, 2-phenylethenyl, 2-pyridylethenyl, mercapto, methylmercapto, ethylmercapto, n-propylmercapto, isopropylmercapto, phenyl, fluorophenyl, difluorophenyl, chlorophenyl, dichlorophenyl, bromophenyl, dibromophenyl, hydroxyphenyl, dihydroxyphenyl, methoxyphenyl, dimethoxyphenyl, mercaptophenyl, bis-mercaptophenyl, methylmercaptophenyl, bis-methylmercapto-phenyl, methylsufinylphenyl, bis-methylsulfinylphenyl, methylsulfonylphenyl, bis-methylsulfonylphenyl, fluoro-hydroxy-phenyl, fluoro-methoxy-phenyl, fluoro-mercapto-phenyl, fluoro-methylmercapto-phenyl, chloro-hydroxy-phenyl, chloro-methoxy-phenyl, chloro-mercapto-phenyl, chloro-methylmercapto-phenyl, bromo-hydroxy-phenyl, bromo-methoxy-phenyl, bromo-mercapto-phenyl, bromo-methylmercapto-phenyl, hydroxy-methoxy-phenyl, hydroxy-mercapto-phenyl, hydroxy-methylmercaptophenyl, methoxy-mercapto-phenyl, methoxy-methylmercapto-phenyl, methoxy-methylsulfinyl-phenyl, cyanophenyl, aminophenyl, amino-dichloro-phenyl, amino-dibromo-phenyl, nitrophenyl, 4-hydroxy-3,5-di-tert.butyl-phenyl, pyridyl, methylpyridyl, ethylpyridyl, isopropylpyridyl, 2-amino-pyrid-5-yl, 2-formylamino-pyrid-5-yl, 2-acetylamino-pyrid-5-yl,2-propionylamino-pyrid-5-yl, 2,6-dichloropyrid-4-yl, 2-chloro-6-amino-pyrid-4-yl, 2-chloro-6-morpholino-pyrid-4-yl, 2,6-dichloro-pyrid-3-yl, 2-chloro-6-morpholino-pyrid-3-yl, pyrrol-2-yl, pyrrol-3-yl, N-methyl-pyrrol-2-yl, N-ethyl-pyrrol-2-yl, N-methyl-pyrrol-3-yl, N-ethyl-pyrrol-3-yl, fur-2-yl, fur-3-yl, 5-methylfur-2-yl, 2-methyl-fur-3-yl, pyrazin-2-yl, pyrimid-2-yl, pyrimid-4-yl, pyrimid-5-yl, benzo[b]fur-2-yl, benzo[b]fur-3-yl, 7-methyl-benzo[b]fur-3-yl, thien-2-yl, thien-3-yl, 5-methylthien-2-yl, 2-methylthien-3-yl, 3-methyl-thien-2-yl, benzo[b]thien-2-yl, benzo[b]thien-3-yl, benzo[b]-thien-4-yl, benzo[b]-thien-5-yl, benzo[b]thien-6-yl benzo[b]-thien-7-yl, pyrazol-3-yl, imidazol-2-yl imidazol-4(5)yl, 1-methyl-imidazol-4-yl, benzo[d]-imidazol-2-yl, oxazol-2-yl, oxazol-4-yl, oxazol-5-yl, 4-methyl-oxazol-5-yl, isoxazol-3-yl, 3-methyl-isoxazol-5-yl, 5-methyl-isoxazol-3-yl, thiazol-2-yl, thiazol-5-yl, 4-methyl-thiazol-5-yl, pyrazol-4-yl, triazol-3-yl, benzo[d]oxazol-2-yl, benzo[d]isoxazol-3-yl, benzo[d]thiazol-2-yl, benzo[d]isothiazol-3-yl, benzo[d]pyrazol-3-yl, indol-2-yl, indol-3-yl, 5-methyl-indol-3-yl, 7-methyl-indol-3-yl, N-methyl-indol-3-yl, quinol-2-yl, isoquinol-1-yl, 2-methyl-quinol-4-yl or 7-methyl-quinol-2-yl group, $R_2$ may represent a hydrogen atom, a methyl, ethyl, n-propyl, isopropyl, n-butyl, isobutyl, tert.butyl, n-pentyl, 1-methyl-n-butyl, 2methyl-n-butyl, 3-methyl-n-butyl, 1-ethyl-n-propyl, tert.pentyl, n-hexyl, benzyl, 1-phenylethyl, 2-phenylethyl, 3-phenylpropyl, 2-hydroxy-ethyl, 2-hydroxy-n-propyl, 3-hydroxy-n-propyl, 1-methyl-2-hydroxy-ethyl, 2-methoxy-ethyl, 2-ethoxy-ethyl, 2-methoxy-n-propyl, 2-n-propoxy-n-propyl, 3-methoxy-n-propyl, 3-ethoxy-n-propyl, 1-methyl-2-methoxy-ethyl or 1-methyl-2-isopropoxy-ethyl group, $R_3$ and $R_4$ may each represent a hydrogen atom or a methyl, ethyl, n-propyl or isopropyl group.

The following compounds, which fall within the scope of protection of the present invention and are not specifically mentioned in the examples, are listed by way of example:

8,8-dimethyl-5-(2-hydroxy-ethyl)-2-(4-pyridyl)-8-hydro-(5H)-imidazo[5,4-g][3,1]benzoxazin-6-one,
8,8-dimethyl-5-(2-hydroxy-ethyl)-2-(3-pyridyl)-8-hydro-(5H)-imidazo[5,4-g][3,1]benzoxazin-6-one,
8,8-dimethyl-2-(2-pyridyl)-8-hydro-(5H)-imidazo[5,4-g][3,1]benzoxazin-6-one,
2-(2-pyridyl)-5,8,8-trimethyl-8-hydro-(5H)-imidazo[5,4g][3,1]benzoxazin-6-one,
5-ethyl-8,8-dimethyl-2-(2-pyridyl)-8-hydro-(5H)-imidazo[5,4-g][3,1]benzoxazin-6-one,
8,8-dimethy-5-(2-methoxy-ethyl)-2-(2-pyridyl)-8-hydro-(5H)-imidazo[5,4-g][3,1]benzoxazin-6-one,
8,8-dimethyl-5-(2-hydroxy-ethyl)-2-(2-pyridyl)-8-hydro-(5H)-imidazo[5,4-g][3,1]benzoxazin-6-one,
8,8dimethyl-2-(4-hydroxyphenyl)-8-hydro-(5H)-imidazo[5,4-g][3,1]benzoxazin-6-one,
5-ethyl-8,8-dimethyl-2-(4-hydroxyphenyl)-8-hydro-(5H)-imidazo-[5,4-g][3,1]benzoxazin-6-one,
8,8-dimethyl-2-(4-hydroxyphenyl)-5-(2-methoxy-ethyl)-8-hydro-(5H)-imidazo[5,4-g][3,1]benzoxazin-6-one,
8,8-dimethyl-5-(2-hydroxy-ethyl)-2-(4-hydroxyphenyl)-8-hydro-(5H)-imidazo[5,4-g][3,1]benzoxazin-6-one,
8,8-dimethyl-5-(2-methoxy-ethyl)-2-(4-methoxyphenyl)-8-hydro-(5H)-imidazo[5,4-g][3,1]benzoxazin-6-one,
8,8-dimethyl-5-(2-hydroxy-ethyl)-2-(4-methoxyphenyl)-8-hydro-(5H)-imidazo[5,4-g][3,1]benzoxazin-6-one,
5-ethyl-2-(4-pyridyl)-8-hydro-(5H)-imidazo[5,4-g][3,1]benzoxazin-6-one,
5-(2-methoxy-ethyl)-2-(4-pyridyl)-8-hydro-(5H)-imidazo[5,4-g][3,1]benzoxazin-6-one,
5-(2-hydroxy-ethyl)-2-(4-pyridyl)-8-hydro-(5H)-imidazo[5,4-g][3,1]benzoxazin-6-one,
2-(3-pyridyl)-8-hydro-(5H)-imidazo[5,4-g][3,1]benzoxazin-6-one,
5-ethyl-2-(3-pyridyl)-8-hydro-(5H)-imidazo[5,4-g][3,1]benzoxazin-6-one,
5-(2-methoxy-ethyl)-2-(3-pyridyl)-8-hydro-(5H)-imidazo[5,4-g][3,1]benzoxazin-6-one,
5-(2-hydroxy-ethyl)-2-(3-pyridyl)-8-hydro-(5H)-imidazo[5,4-g][3,1]benzoxazin-6-one,
2-(2-pyridyl)-8-hydro-(5H)-imidazo[5,4-g][3,1]benzoxazin-6-one,
5-methyl-2-(2-pyridyl)-8-hydro-(5H)-imidazo[5,4-g][3,1]benzoxazin-6-one,
5-ethyl-2-(2-pyridyl)-8-hydro-(5H)-imidazo[5,4-g][3,1]benzoxazin-6-one,
5-(2-methoxy-ethyl)-2-(2-pyridyl)-8-hydro-(5H)-imidazo[5,4-g][3,1]benzoxazin-6-one,
5-(2-hydroxy-ethyl)-2-(2-pyridyl)-8-hydro-(5H)-imidazo[5,4-g][3,1]benzoxazin-6-one,
2-(4-hydroxyphenyl)-8-hydro-(5H)-imidazo[5,4-g][3,1]benzoxazin-6-one,
2-(4-hydroxyphenyl)-5-methyl-8-hydro-(5H)-imidazo[5,4-g][3,1]benzoxazin-6-one,
5-ethyl-2-(4-hydroxyphenyl)-8-hydro-(5H)-imidazo[5,4-g][3,1]benzoxazin-6-one,
2-(4-hydroxyphenyl)-5-(2-methoxy-ethyl)-8-hydro-(5H)-imidazo[5,4-g][3,1]benzoxazin-6-one,
5-(2-hydroxy-ethyl)-2-(4-hydroxyphenyl)-8-hydro-(5H)-imidazo[5,4-g][3,1]benzoxazin-6-one,
2-(4-methoxyphenyl)-8-hydro-(5H)-imidazo[5,4-g][3,1]benzoxazin-6-one,
5-ethyl-2-(4-methoxyphenyl)-8-hydro-(5H)-imidazo[5,4-g][3,1]benzoxazin-6-one,
5-(2-methoxy-ethyl)-2-(4-methoxyphenyl)-8-hydro-(5H)-imidazo[5,4-g][3,1]benzoxazin-6-one,
5-(2-hydroxy-ethyl)-2-(4-methoxyphenyl)-8-hydro-(5H)-imidazo[5,4-g][3,1]benzoxazin-6-one,
8-methyl-2-(4-pyridyl)-8-hydro-(5H)-imidazo[5,4-g][3,1]benzoxazin-6-one,
5,8-dimethyl-2-(4-pyridyl)-8-hydro-(5H)-imidazo[5,4-g][3,1]benzoxazin-6-one,
5-ethyl-8-methyl-2-(4-pyridyl)-8-hydro-(5H)-imidazo[5,4-g][3,1]benzoxazin-6-one,
5-(2-methoxy-ethyl)-8-methyl-2-(4-pyridyl)-8-hydro-(5H)-imidazo[5,4-g][3,1]benzoxazin-6-one,
5-(2-hydroxy-ethyl)-8-methyl-2-(4-pyridyl)-8-hydro-(5H)-imidazo[5,4-g][3,1]benzoxazin-6-one,
8-methyl-2-(3-pyridyl)-8-hydro-(5H)-imidazo[5,4-g][3,1]benzoxazin-6-one,
5,8-dimethyl-2-(3-pyridyl)-8-hydro-(5H)-imidazo[5,4-g][3,1]benzoxazin-6-one,
5-ethyl-8-methyl-2-(3-pyridyl)-8-hydro-(5H)-imidazo[5,4-g][3,1]benzoxazin-6-one,
5-(2-methoxy-ethyl)-8-methyl-2-(3-pyridyl)-8-hydro-(5H)-imidazo[5,4-g][3,1]benzoxazin-6-one,
5-(2-hydroxy-ethyl)-8-methyl-2-(3-pyridyl)-8-hydro-(5H)-imidazo[5,4-g][3,1]benzoxazin-6-one,
8-methyl-2-(2-pyridyl)-8-hydro-(5H)-imidazo[5,4-g][3,1]benzoxazin-6-one,
5,8-dimethyl-2-(2-pyridyl)-8-hydro-(5H)-imidazo[5,4-g][3,1]benzoxazin-6-one,
5-ethyl-8-methyl-2-(2-pyridyl)-8-hydro-(5H)-imidazo[5,4-g][3,1]benzoxazin-6-one,
5-(2-methoxy-ethyl)-8-methyl-2-(2-pyridyl)-8-hydro-(5H)-imidazo[5,4-g][3,1]benzoxazin-6-one,
5-(2-hydroxy-ethyl)-8-methyl-2-(2-pyridyl)-8-hydro-(5H)-imidazo[5,4-g][3,1]benzoxazin-6-one,
2-(4-hydroxyphenyl)-8-methyl-8-hydro-(5H)-imidazo[5,4-g][3,1]benzoxazin-6-one,
5,8-dimethyl-2-(4-hydroxyphenyl)-8-hydro-(5H)-imidazo[5,4-g][3,1]benzoxazin-6-one,
5-ethyl-2-(4-hydroxyphenyl)-8-methyl-8-hydro-(5H)-imidazo[5,4-g][3,1]benzoxazin-6-one,
2-(4-hydroxyphenyl)-5-(2-methoxy-ethyl)-8-methyl-8-hydro-(5H)-imidazo[5,4-g][3,1]benzoxazin-6-one,
5-(2-hydroxy-ethyl)-2-(4-hydroxyphenyl)-8-methyl-8-hydro-(5H)-imidazo[5,4-g][3,1]benzoxazin-6-one,
2-(4-methoxyphenyl)-8-methyl-8-hydro-(5H)-imidazo[5,4-g][3,1]benzoxazin-6-one,
5,8-dimethyl-2-(4-methoxyphenyl)-8-hydro-(5H)-imidazo[5,4-g][3,1]benzoxazin-6-one,
5-ethyl-2-(4-methoxyphenyl)-8-methyl-8-hydro-(5H)imidazo[5,4-g][3,1]benzoxazin-6-one,
5-(2-methoxy-ethyl)-2-(4-methoxyphenyl)-8-methyl-8-hydro-(5H)-imidazo[5,4-g][3,1]benzoxazin-6-one and
5-(2-hydroxy-ethyl)-2-(4-methoxyphenyl)-8-methyl-8-hydro-(5H)-imidazo[5,4-g][3,1]benzoxazin-6-one,
the 3H-tautomers and acid addition salts thereof.

The preferred compounds of formula I above are, however, those wherein $R_1$ represents an alkyl group with 1 or 2 carbon atoms optionally substituted by a phenyl or pyridyl group; an alkyl group with 3 to 5 carbon atoms; a mercapto group optionally substituted by a methyl group; a vinyl group substituted in the end position by a phenyl or pyridyl group; a phenyl group optionally substituted by a hydroxy, methoxy, methylmercapto, methylsulfinyl, methylsulfonyl, cyano or nitro group; a dimethoxyphenyl, 3,5-di-tert.butyl-4-hydroxy-phenyl, 4-amino-3,5-dihalo-phenyl, pyridyl, piperidinyl, morpholinopyridyl, quinolyl, furanyl, thienyl or pyrazinyl group, $R_2$ represents a hydrogen atom, a methyl, benzyl, ethyl, n-propyl, isopropyl, 2-hydroxyethyl or 2-methoxyethyl group, $R_3$ and $R_4$, which may be identical or different, represent hydrogen atoms, methyl or ethyl groups, the 3H-tautomers and the acid addition salts thereof.

However, particularly preferred compounds of formula I are those wherein $R_1$ represents an alkyl group with 1 to 3 carbon atoms or a pyridyl, pyrazinyl, furyl or thienyl group, $R_2$ represents a hydrogen atom or a methyl or ethyl group, $R_3$ and $R_4$ each represent a methyl group, the 3H-tautomers and acid addition salts thereof.

According to the invention the new compounds are obtained by the following processes:

(a) cyclising a compound of formula

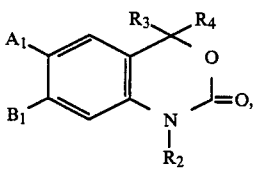

wherein $R_2$ to $R_4$ are as hereinbefore defined, one of the groups $A_1$ or $B_1$ represents an $NH_2$ group and the other group $A_1$ or $B_1$ represents a

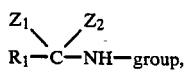

group, wherein $R_1$ is defined as hereinbefore, $Z_1$ and $Z_2$, which may be identical or different, represent nucleophilically exchangeable groups such as optionally substituted amino, alkoxy, phenylalkoxy, phenoxy, alkylmercapto, phenylalkylmercapto or phenylthio groups or $Z_1$ and $Z_2$ together represent an oxygen or sulphur atom, an imino group optionally substituted by an alkyl or phenylalkyl group, whilst the above-mentioned alkyl moieties may each contain from 1 to 3 carbon atoms, or an alkylenedioxy group with 2 or 3 carbon atoms.

$Z_1$ and $Z_2$ may, for example, each represent a methoxy, ethoxy, propoxy, benzyloxy, methylmercapto, ethylmercapto, propylmercapto, phenylmercapto or benzylmercapto group or $Z_1$ and $Z_2$ together with the carbon atom may represent carbonyl or thiocarbonyl group.

The reaction is conveniently carried out in a solvent or mixture of solvents such as ethanol, isopropanol, glacial acetic acid, tetrahydrofuran, dioxane, benzene, toluene, xylene, chlorobenzene, glycol, glycolmonomethylether, glycoldimethylether, diethylene-glycoldimethylether, dimethylformamide, tetralin or sulfolan, optionally in the presence of a condensation agent such as phosphorus oxychloride, thionyl chloride, sulfuryl chloride, hydrochloric acid, sulfuric acid, phosphoric acid, polyphosphoric acid, p-toluenesulfonic acid, glacial acetic acid, acetic acid anhydride, N,N'-dicyclohexylcarbodiimide, carbonyldiimidazole, potassium methoxide or potassium tertbutoxide at temperatures of between 0° and 300° C., but preferably at the boiling temperature of the reaction mixture, e.g. at temperatures of between 50° and 285° C. However, the reaction may also be carried out in a melt.

However, it is particularly advantageous to carry out the reaction by preparing a starting compound of formula II in the reaction mixture by reduction of a corresponding nitro compound of formula

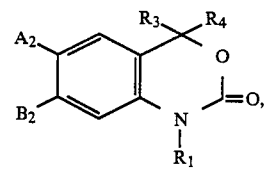

wherein $R_2$, $R_3$ and $R_4$ are as hereinbefore defined, one of the groups $A_2$ or $B_2$ is a nitro group and the other group $A_2$ or $B_2$ represents a group of formula

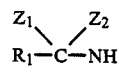

wherein $R_1$, $Z_1$ and $Z_2$ are as hereinbefore defined, or by reaction of a compound of formula

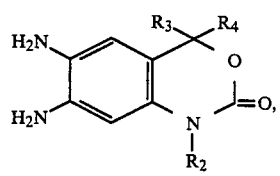

wherein $R_2$, $R_3$, and $R_4$ are as hereinbefore defined, with a reactive derivative of a carboxylic acid of formula

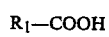

wherein $R_1$ is as hereinbefore defined, such as the nitrile, anhydride, ester, thioester, orthoester, halide, methoiodide, amide or thioamide thereof. The reduction of a nitro group is preferably carried out in a suitable solvent such as glacial acetic acid, water, ethanol or water/glacial acetic acid, conveniently with nascent hydrogen, e.g. in the presence of zinc/glacial acetic acid, tin/hydrochloric acid or tin(II)chloride/hydrochloric acid, or with catalytically activated hydrogen, e.g. with hydrogen in the presence of platinum, palladium or Raney nickel, at temperatures of between 0° and 150° C., preferably at temperatures between 20° and 125° C. Any double bond present in the group $R_1$ may be reduced at the same time.

The acylation is appropriately carried out in a solvent such as methylene chloride, chloroform, carbon tetrachloride, ether, tetrahydrofuran, dioxane, benzene, toluene, acetonitrile or dimethylformamide, optionally in the presence of an acid-activating agent or a dehydrating agent, e.g. in the presence of ethyl chloroformate, thionyl chloride, phosphorus trichloride, phosphorus pentoxide, N,N'-dicyclohexylcarbodiimide, N,N'-dicyclohexylcarbo diimide/N-hydroxysuccinimide, N,N'-carbonyldiimidazole or N,N'-thionyldiimidazole or triphenylphosphine/carbon tetrachloride, or an agent which activates the amino group, e.g. phosphorus trichloride, and optionally in the presence of an inorganic base such as sodium carbonate or a tertiary organic base such as triethylamine or pyridine, which may simultaneously be used as solvent, at temperatures of between −25° C. and 250° C., but preferably at temperatures of between −10° C. and the boiling temperature of the solvent used. The reaction may also be carried out without a solvent and furthermore any water formed during the reaction may be removed by azeotropic distillation, e.g. by heating with toluene using a water separator, or by adding a drying agent such as magnesium sulphate or a molecular sieve.

(b) Reaction of a compound of formula

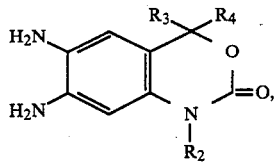   (IV)

wherein $R_2$, $R_3$ and $R_4$ are as hereinbefore defined, with an aldehyde of formula

   (VI)

wherein $R_1$ is as hereinbefore defined, and subsequent oxidation.

The reaction of a compound of formula IV with an aldehyde of formula VI is conveniently carried out in a suitable solvent such as methanol, ethanol, glacial acetic acid or ethylene chloride at temperatures between 20° and 100° C. The subsequent oxidation is carried out with an oxidizing agent such as oxygen, hydrogen peroxide or a peracid such as m-chloroperbenzoic acid at temperatures between 20° and 100° C., preferably at temperatures between 40° and 80° C.

If according to the invention a compound of formula I is obtained wherein $R_2$ represents a hydrogen atom and/or $R_1$ represents a hydroxy or mercapto group, this may be converted by alkylation into the corresponding alkyl compound and/or if a compound of formula I is obtained wherein $R_1$ is a vinyl group substituted by a phenyl or pyridyl group in the end position, this may be converted by catalytic hydrogenation into a corresponding compound of formula I wherein $R_1$ represents an ethylene group substituted by a phenyl or pyridyl group in the end position, and/or a compound of formula I wherein $R_2$ represents a benzyl group may be converted by catalytic hydrogenation into a corresponding compound of formula I wherein $R_2$ represents hydrogen, and/or a compound of formula I wherein $R_1$ represents a pyridine ring may be converted by catalytic hydrogenation into a corresponding compound of formula I wherein R represents a piperidinyl group and/or a compound of formula I wherein $R_1$ represents an alkoxyphenyl or dialkoxyphenyl group may be converted by ether cleavage into a corresponding compound of formula I wherein $R_1$ represents a hydroxyphenyl or dihydroxyphenyl group and/or a compound of formula I wherein $R_1$ represents an alkylmercaptophenyl or dialkylmercaptophenyl group may be converted by oxidation into a corresponding compound of formula I wherein $R_1$ represents an alkylsulfinyl, alkylsulphonyl, dialkylsulphinyl or dialkylsulfonyl phenyl group.

The subsequent alkylation is carried out in a suitable solvent such as methanol, ethanol, diethylether, acetone, methylene chloride, tetrahydrofuran, dioxane, dimethylformamide or dimethylsulfoxide, optionally in the presence of a base such as sodium carbonate, potassium tert.butoxide, triethylamine or pyridine, whilst the latter two may simultaneously serve as solvent, with a suitbble alkylating agent such as methyliodide, dimethylsulfate, ethylbromide, diethylsulfate, n-propylbromide, isopropylbromide, ethylene oxide, 2-hydroxyethylbromide or formaldehyde/formic acid or in the presence of sodium cyanoborohydride, if a corresponding carbonyl compound is used, at temperatures between 0° and 100° C.

The subsequent catalytic hydrogenation is preferably carried out with hydrogen in the presence of a hydrogenation catalyst such as platinum, palladium/charcoal or Raney nickel in a suitable solvent, e.g. in methanol, ethanol, tetrahydrofuran, dioxane, glacial acetic acid, dimethylformamide or ethylacetate, at temperatures between 20° and 100° C., preferably at 20° to 50° C.

The subsequent ether cleavage is conveniently carried out in the presence of an acid such as hydrochloric acid, sulfuric acid, phosphoric acid or boron tribromide in a suitable solvent such as ethylene chloride at temperatures between −10° C. and the boiling temperature of the solvent used, preferably at temperatures between 0° and 50° C.

The subsequent oxidation is preferably carried out in a solvent or mixture of solvents, e.g. in water, water/pyridine, methanol, ethanol, acetone, formic acid, glacial acetic acid, dilute sulfuric acid or trifluoroacetic acid, at temperatures of between −80° and 100° C. depending on the oxidizing agent used.

In order to prepare an alkylsulfinyl compound of formula I, oxidation is conveniently carried out with one equivalent of the oxidizing agent used, e.g. with hydrogen peroxide in glacial acetic acid or formic acid at 0° to 20° C. or in acetone at 0° to 60° C., with a peracid such as performic acid or m-chloroperbenzoic acid in glacial acetic acid or trifluoroacetic acid at 0° to 20° C., with sodium metaperiodate in aqueous methanol or ethanol at 15° to 25° C. or with ter.butylhypochlorite in methanol at −80° to −30° C.

In order to prepare an alkylsulfonyl compound of formula I oxidation is conveniently carried out with one or more equivalents of the oxidizing agent used, e.g. with hydrogen in glacial acetic acid or in formic acid at 20° to 100° C. or in acetone at 0° to 60° C., with a peracid such as performic acid or m-chloroperbenzoic acid in glacial acetic acid, trifluoroacetic acid or chloroform at 0° to 50° C., or with bromic acid or potassium permanganate in glacial acetic acid, water/sulfuric acid or in acetone at 0° to 20° C. Thus, if a compound of formula I used contains an alkylmercapto group, subsequent oxidation is preferably carried out with two or more equivalents of the oxidizing agent in question and, accordingly, with at least one equivalent if a compound of formula I used contains an alkylsulfinyl group.

Moreover, the compounds of general formula I obtained may be converted into their acid addition salts, particularly their physiologically acceptable salts with inorganic or organic acids for pharmaceutical use. Suitable acids include, for example, hydrochloric, hydrobromic, sulfuric, phosphoric, fumaric, succinic, lactic, citric, tartaric and maleic acids.

The compounds of general formulae II to VI used as starting material are obtained by methods known from the literature.

Thus, for example, 4,4-dimethyl-6-isonicotinoylamino-7-nitro-4H-3,1-benzoxazin-2-one is obtained by reacting methyl anthranilate with methyl magnesium iodide in ethereal solution to obtain o-aminophenyl-dimethylcarbinol, which is cyclised by reacting with phosgene in a mixture of toluene and chloroform as solvent in the presence of solid potassium carbonate to obtain 4,4-dimethyl-4H-3,1-benzoxazin-2-one. By subsequent nitration with fuming nitric acid (d=1.52), 4,4-dimethyl-6-nitro-benzoxazin-2-one is obtained which is converted by catalytic hydrogenation in the presence of Raney nickel in dimethyl formamide into 6-amino-4,4-dimethyl-4H-3,1-benzoxazin-2-one. By inserting an acetyl protecting group by means of acetic anhydride, the precondition for further nitration with fuming nitric acid (d=1.52) is created in the 7- position of the molecule. The acetyl protecting group is split off again from the resulting 6-acetamido-4,4-dimethyl-7-nitro-4H-3, 1-benzoxazin-2-one by treating with concentrated hydrochloric acid in isopropanol, and the resulting 6-amino-4,4-dimethyl-7-nitro-4H-3,1-benzoxazin-2-one is converted into 4,4-dimethyl-6-isonicotinoylamido-7-nitro-4H-3,1-benzoxazin-2-one by treating with isonicotic acid chloride in pyridine as solvent.

The new compounds of formula I, the optically active antipodes and the acid addition salts thereof, particularly the physiologically acceptable acid addition salts with inorganic or organic acids, have valuable pharmacological properties, as already mentioned hereinbefore, particularly cardiovascular effects, namely a cardiotonic activity and an antithrombotic activity, whilst having little effect on blood pressure.

For example, the following compounds:
A = 8,8-dimethyl-2-(4-pyridyl)-8-hydro-(5H)-imidazo[5,4-g][3,1]benzoxazin-6-one,
B = 5-ethyl-8,8-dimethyl-2-(4-pyridyl)-8-hydro-(5H)imidazo[5,4-g][3,1]benzoxazin-6-one,
C = 8,8-dimethyl-2-n-propyl-8-hydro-(5H)-imidazo[5,4-g][3,1]benzoxazin-6-one,
D = 5-ethyl-8,8-dimethyl-2-(2-furyl)-8-hydro-(5H)imidazo[5,4-g][3,1]benzoxazin-6-one,
E = 8,8-dimethyl-2-(2-furyl)-8-hydro-(5H)-imidazo[5,4-g][3,1]benzoxazin-6-one and
F = 8,8-dimethyl-2-(2-thienyl)-8-hydro-(5H)-imidazo[5,4-g][3,1]benzoxazin-6-one, were tested for their biological properties as follows:

1. Determination of the effect on blood pressure and positive inotropic activity in anaesthetized cats: The tests were carried out on cats which had been anaesthetized with sodium pentobarbital (40 mg/kg i.p. and 8 mg/kg/hour i.v.). The animals breathed spontaneously. The arterial blood pressure was measured in the aorta abdominalis using a Statham pressure transducer (P 23 Dc). To determine the positive inotropic activity the pressure in the left ventricle was measured using a catheter-tip manometer (Millar PC-350 A). From this, the contractility parameter $dp/dt_{max}$ was obtained using an analogue differentiator. The test substance was injected into a vena femoralis. Polydiol 200 was used as solvent. The substance was tested on 2 cats, dosage 0.3 mg/kg i.v.

The following Table contains the average values:

| Substance | Dosage mg/kg i.v. | Diastolic blood Pressure change in mmHg | Increase of dp/dt in % | Duration of effect (half life) |
|---|---|---|---|---|
| A | 0.3 | 0 | +43 | 18 minutes |
| B | 0.3 | −21 | +52 | 16 minutes |
| C | 0.3 | −11 | +31 | 11 minutes |
| D | 0.3 | −37 | +41 | 4 minutes |
| E | 0.3 | −16 | +31 | 7 minutes |
| F | 0.3 | −24 | +28 | 10 minutes |

In this connection it should be pointed out that no toxic side effects were observed in the biological tests on the substances.

In view of their pharmacological properties, the compounds of general formula I prepared according to the invention and their optically active antipodes and physiologically acceptable acid addition salts with inorganic or organic acids are suitable for the treatment of chronic and acute cardiac insufficiency of various origins and/or for the prevention of arterial thromboembolism and diseases of arterial occlusion.

For this purpose, the new compounds, possibly combined with other active substances, may be incorporated in conventional pharmaceutical preparations such as plain or coated tablets, powders, suspensions, suppositories or ampoules. The single dosage is 1 to 50 mg, preferably 2 to 40 mg administered intravenously and 5–150 mg, preferably 5 to 100 mg by oral route, 1 to 4 times a day in adults.

The following Examples are intended to illustrate the invention:

EXAMPLE A

4,4-Dimethyl-4H-3,1-benzoxazin-2-one

At 15°–25° C. a solution of 226 g (1.5 mol) of methyl anthranilate in 1 liter of ether is added dropwise to a methyl magnesium iodide solution prepared from 170 g (7 mol) of magnesium chips, 993 g (7 mol) of methyl iodide in 3.5 liters of ether. After stirring for 1.5 hours the reaction mixture is poured onto ice water containing ammonium chloride, the ether phase is separated off, the aqueous phase is extracted again with ether and the combined ether phases are washed with ammonium chloride solution, dried with sodium sulphate and the ether is distilled off. The o-aminophenyldimethylcarbinol thus obtained is further reacted without being purified: it is dissolved in 1.5 liters of chloroform to which 5 ml of water have been added and then 300 g (2.2 mol) of potassium carbonate are added. 800 ml (1.6 mol) of a 20% solution of phosgene in toluene is carefully added dropwise thereto over a period of 2 hours, whereupon the temperature rises to 60° C. After the mixture has been left to stand overnight, 1 liter of water is added, the mixture is extracted with chloroform, the chloroform phase is washed and dried and the solvent is distilled off. The residue is recrystallized from 1.7 liters of cyclohexane.

Yield: 234.2 g (88.4% of theory),
Melting point: 107°–108° C.

The following were prepared analogously:
4,4-diethyl-4H-3,1-benzoxazin-2-one from methyl anthranilate, ethyl magnesium bromide and phosgene,
4H-3,1-benzoxazin-2-one from methyl anthranilate, lithium aluminium hydride and phosgene.

EXAMPLE B

4,4-Dimethyl-6-nitro-4H-3,1-benzoxazin-2-one 234.1 g (1.32 mol) of 4,4dimethyl-4H-3,1-benzoxazin-2-one are added in batches to 793 ml of fuming nitric acid (d=1.51) at −40° C. over a period of ¾ hour with stirring and the mixture is stirred for a further ¾ hour at −40° C. The reaction mixture is then poured into 3½ liters of ice water, the precipitate is suction filtered, washed with water, dried and recrystallized from butanol/dimethylformamide.

Yield: 251 g (85.6% of theory),
Melting point: 244°–246° C.
The following were prepared analogously:
4,4-diethyl-6-nitro-4H-3,1-benzoxazin-2-one,
6-nitro-4H-3,1-benzoxazin-2-one.

EXAMPLE C

6-Amino-4,4-dimethyl-4H-3,1-benzoxazin-2-one 251 g (1.13 mol) of 4,4-dimethyl-6-nitro-4H-3,1-benzoxazin-2-one are dissolved in 1250 ml of dimethylformamide, 30 g of Raney nickel are added and the mixture is hydrogenated at 60° C. in an autoclave initially for 3 hours at 15 bar and then for 6 hours at 60 bar of hydrogen pressure. The catalyst is removed by suction filtering, the solvent is distilled off and the residue is recrystallized from isopropanol/diisopropylether.

Yield: 205.9 g (94.8% of theory),
Melting point: 171°–172° C.
The following were prepared analogously:
6-amino-4,4-diethyl-4H-3,1-benzoxazin-2-one,
6-amino-4H-3,1-benzoxazin-2-one.

EXAMPLE D

6-Acetamido-4,4-dimethyl-4H-3,1-benzoxazin-2-one 122.2 g (0.636 mol) of 6-amino-4,4-dimethyl-4H-3,1-benzoxazin-2-one are dissolved in 800 ml of glacial acetic acid and 120 ml of acetic anhydride are added. The temperature rises to 35° C. The mixture is stirred for a further ½ hour, 1 liter of ether is added and the precipitate is suction filtered and washed with ether.

Yield: 141.3 g (94.9% of theory),
Melting point: 222°–223° C.
The following were prepared analogously:
6-acetamido-4,4-diethyl-4H-3,1-benzoxazin-2-one,
6-acetamido-4H-3,1-benzoxazin-2-one.

EXAMPLE E

6-Amino-4,4-dimethyl-7-nitro-4H-3,1-benzoxazin-2-one 141.3 g (0.6 mol) of 6-acetamido-4,4-dimethyl-4H-3,1-benzoxazin-2-one are added in batches to 360 ml of fuming nitric acid (d=1.53) at −40° C. within ¾ hour with stirring and the resulting mixture is stirred for a further 1.5 hours at −35° C. The reaction mixture is poured onto ice, the precipitate is suction filtered, washed with water and, in order to cleave the acetyl group, refluxed for 3 hours in a mixture of 500 ml of isopropanol, 500 ml of water and 250 ml of concentrated hydrochloric acid. After cooling, ice water is added, the precipitate is suction filtered, washed with water and dried.

Yield: 112 g (78.3% of theory),
Melting point: from 257° C. (decomp.)
The following were prepared analogously:
6-amino-4,4-diethyl-7-nitro-4H-3,1-benzoxazin-2-one,
6-amino-7-nitro-4H-3,1-benzoxazin-2-one.

EXAMPLE F

4,4-Dimethyl-6-isonicotinoylamido-7-nitro-4H-3,1-benzoxazin-2-one

A solution of 4.75 g (0.02 mol) of 6-amino-4,4-dimethyl-7-nitro-4H-3,1-benzoxazin-2-one and 4.75 g (0.02 mol) of isonicotinic acid chloride in 50 ml of pyridine is stirred for 1 hour at 50° C. Then ice water is added, the precipitate is suction filtered, washed with water and recrystallized from butanol/dimethylformamide.

Yield: 5.94 g (86.7% of theory),
Melting point: 265°–267° C.
The following were prepared analogously:
6-isonicotinoylamido-7-nitro-1,4,4-trimethyl-4H-3,1-benzoxazin-2-one
Melting point: 232°–233° C.
6-nicotinoylamido-7-nitro-1,4,4-trimethyl-4H-3,1-benzoxazin-2-one
Melting point: 224°–226° C.
4,4-dimethyl-6-nicotinoylamido-7-nitro-4H-3,1-benzoxazin-2-one
Melting point: 277°–279° C.
6-(4-methoxy-benzoylamido)-7-nitro-1,4,4-trimethyl-4H-3,1-benzoxazin-2-one
Melting point: 193°–195° C.
4,4-dimethyl-6-(4-methoxy-benzoylamido)-7-nitro-4H-3,1-benzoxazin-2-one
Melting point: 300° C.
1-ethyl-4,4-dimethyl-6-isonicotinoylamido-7-nitro-4H-3,1-benzoxazin-2-one
Melting point: 196°–197° C.
4,4-dimethyl-6-isonicotinoylamido-1-(2-methoxy-ethyl)-7-nitro-4H-3,1-benzoxazin-2-one
Melting point: 186°–188° C.
6-benzoylamido-4,4-dimethyl-7-nitro-4H-3,1-benzoxazin-2-one
Melting point: from 287° C. (decomp.)
4,4-dimethyl-1-(2-methoxy-ethyl)-6-nicotinoylamido-7-nitro-4H-3,1-benzoxazin-2-one
Melting point: 140° C. (decomp.)
4,4-dimethyl-1-isopropyl-6-isonicotinoylamido-7-nitro-4H-3,1-benzoxazin-2-one
Melting point: 254°–256° C. (decomp.) 4,4-dimethyl-1-isopropyl-6-nicotinoylamido-7-nitro-4H-3,1-benzoxazin-2-one
Melting point: 177°–178° C.
1-benzyl-4,4-dimethyl-6-isonicotinoylamido-7-nitro-4H-3,1-benzoxazin-2-one
Melting point: 181°–182° C.
1-benzyl-4,4-dimethyl-6-nicotinoylamido-7-nitro-4H-3,1-benzoxazin-2-one
Melting point: 186°–187° C.
1-benzyl-4,4-dimethyl-6-(4-methoxy-benzoylamido)-7-nitro-4H-3,1-benzoxazin-2-one
Melting point: 156°–157° C.
4,4-dimethyl-6-isonicotinoylamido-1-n-propyl-7-nitro-4H-3,1-benzoxazin-2-one
Melting point: 221°–222° C.
4,4-dimethyl-6-(4-methoxy-benzoylamido)-7-nitro-1-n-propyl-4H-3,1-benzoxazin-2-one
Melting point: 201°–202° C.
4,4-dimethyl-6-nicotinoylamido-7-nitro-1-n-propyl-4H-3,1-benzoxazin-2-one
Melting point: 164°–165° C.

1-n-butyl-4,4-dimethyl-6-(4-methoxy-benzoylamido)-7-nitro-4H-3,1-benzoxazin-2-one
Melting point: 174°–175° C.

1-n-butyl-4,4-dimethyl-6-isonicotinoylamido-7-nitro-4H-3,1-benzoxazin-2-one
Melting point: 171°–172° C.

1-n-butyl-4,4-dimethyl-6-nicotinoylamido-7-nitro-4H-3,1-benzoxazin-2-one
Melting point: 152°–153° C.

1-ethyl-4,4dimethyl-6-(4-methoxy-benzoylamido)-7-nitro-4H-3,1-benzoxazin-2-one
Melting point: 176°–178° C.

1-ethyl-4,4-dimethyl-6-nicotinoylamido-7-nitro-4H-3,1-benzoxazin-2-one
Melting point: 188°–189° C.

4,4-dimethyl-6-(3,5-di-tert.butyl-4-hydroxy-benzoylamido)-7-nitro-4H-3,1-benzoxazin-2-one
Melting point: 290° C.

1-ethyl-4,4-dimethyl-6-(3,5-di-tert.butyl-4-hydroxy-benzoylamido)-7-nitro-4H-3,1-benzoxazin-2-one
Melting point: 234°–235° C.

6-(3,5-di-tert.butyl-4-hydroxy-benzoylamido)-7-nitro-1,4,4-trimethyl-4H-3,1-benzoxazin-2-one
Melting point: 247°–248° C.

6-isonicotinoylamido-7-nitro-4H-3,1-benzoxazin-2-one
Melting point 290° C. (decomp.)

6-benzoylamido-7-nitro-4H-3,1-benzoxazin-2-one
Melting point: oil 6-acetamido-7-nitro-4H-3,1-benzoxazin-2-one
Melting point: from 250° C. (decomp.)

6-isonicotinoylamido-1-methyl-7-nitro-4H-3,1-benzoxazin-2-one
Melting Point: 208°–209° C 6-nicotinoylamido-1-methyl-7-nitro-4H-3,1-benzoxazin-2-one
Melting point: 230°–231° C.

1-methyl-6-(4-methoxy-benzoylamido)-7-nitro-4H-3,1-benzoxazin-2-one
Melting point: 207°–208° C.

4,4-diethyl-6-(4-methoxy-benzoylamido)-7-nitro-4H-3,1-benzoxazin-2-one
Melting point: 205°–207° C.

4,4-diethyl-6-isonicotinoylamido-7-nitro-4H-3,1-benzoxazin-2-one
Melting point: 197°–199° C.

4,4-diethyl-6-nicotinoyl-amido-7-nitro-4H-3,1-benzoxazin-2-one
Melting Point: 108°–110° C.

4,4-diethyl-1-methyl-6-isonicotinoylamido-7-nitro-4H-3,1-benzoxazin-2-one
Melting Point: 190°–192° C.

4,4-diethyl-6-(4-methoxy-benzoylamido)-1-methyl-7-nitro-4H-3,1-benzoxazin-2-one
Melting point: 176°–177° C.

4,4-diethyl-1-methyl-6-nicotinoylamido-7-nitro-4H-3,1-benzoxazin-2-one
Melting point: 143°–144° C.

6-isonicotinoylamido-7-nitro-1,4,4-triethyl-4H-3,1-benzoxazin-2-one
Melting Point: 179°–180° C.

6-nicotinoylamido-7-nitro-1,4,4-triethyl-4H-3,1-benzoxazin-2-one
Melting Point: 162°–163° C.

6-(4-methoxy-benzoylamido)-7-nitro-1,4,4-triethyl-4H-3,1-benzoxazin-2-one
Melting point: 144°–145° C.

4,4-dimethyl-6-(2-phenyl-propionylamido)-7-nitro-4H-3,1-benzoxazin-2-one
Melting point: 220°–222° C.

6-(2,4-dimethoxy-benzoylamido-4,4-dimethyl-7-nitro-4H-3,1-benzoxazin-2-one
Melting Point: 257°–259° C.

4,4-dimethyl-7-nitro-6-phenylacetamido-4H-3,1-benzoxazin-2-one
Melting point: 240°–242° C.

6-butyrylamino-4,4-dimethyl-7-nitro-4H-3,1-benzoxazin-one
Melting Point: 281° C.

4,4-dimethyl-6-(2-methyl-valerylamido)-7-nitro-44H-3,1-benzoxazin-2-one
Melting Point: 184°–185° C.

4,4-dimethyl-6-(4-methylsulphonyl-benzoylamido)-7-nitro-4H-3,1-benzoxazin-2-one
Melting Point: from 270° C. (decomp.)

6-(4-amino-3,5-dibromo-benzoylamido)-4,4-dimethyl-7-nitro-4H-3,1-benzoxazin-2-one
Melting point: 286°–288° C.

1-ethyl-6-(4-amino-3,5-dibromo-benzoylamido)-4,4-dimethyl-7-nitro-4H-3,1-benzoxazin-2-one
Melting Point: 216°–218° C.

6-(4-amino-3,5-dichloro-benzoylamido)-4,4-dimethyl-7-nitro-4H-3,1-benzoxazin-2-one
Melting Point: from 288° C.

1-ethyl-6-(4-amino-3,5-dichloro-benzoylamido)-4,4-dimethyl-7-nitro-4H-3,1-benzoxazin-2-one
Melting point: 246°–247° C.

6-(4-quinolin-carbonamido)-4,4-dimethyl-7-nitro-4H-3,1-benzoxazin-2-one
Melting point: 269°–270° C.

1-ethyl-4,4-dimethyl-6-(2-thenoylamido)-7-nitro-4H-3,1-benzoxazin-2-one
Melting point: 177°–179° C.

1-ethyl-4,4-dimethyl-6-(2-furoylamido)-7-nitro-4H-3,1-benzoxazin-2-one
Melting Point: 215°–217° C.

4,4-dimethyl-6-(2-furoylamido)-7-nitro-4H-3,1-benzoxazin-2-one
Melting Point: 263°–265° C.

4,4-dimethyl-7-nitro-6-(2-thenoylamido)-4H-3,1-benzoxazin-2-one
Melting point: from 227° C.

4,4-dimethyl-6-(4-methylmercapto-benzoylamido)-7-nitro-4H-3,1-benzoxazin-2-one
Melting point: 292°–294° C.

4,4-dimethyl-7-nitro-6-[3-(4-pyridyl)-propionylamido]-4H-3,1-benzoxazin-2-one
Melting point: 257°–258° C.

4,4-dimethyl-6-(2-morpholino-nicotinoylamido)-7-nitro-4H-3,1-benzoxazin-2-one
Melting point: 257°–259° C.

4,4-dimethyl-7-nitro-6-(2-pyrazinoylamido)-4H-3,1-benzoxazin-2-one
Melting point >300° C.

4,4-dimethyl-1-isopropyl-6-(4-methoxy-benzoylamido)-7-nitro-4H-3,1-benzoaxzin-2-one
Melting point: 179°–181° C.

6-(4-cyan-benzoylamidol-4,4-dimethyl-7-nitro-4H-3,1-benzoaxzin-2-one
Melting point: 276°–278° C.

4,4-dimethyl-6-(3-furoylamido)-7-nitro-4H-3,1-benzoxazin-2-one
Melting point: 252°–253° C.

1-ethyl-4,4-dimethyl-6-(3-furoylamido)-7-nitro-4H-3,1-benzoxazin-2-one
Melting point: 206°–208° C.

4,4-dimethyl-7-nitro-6-(3-thenoylamido)-4H-3,1-benzoxazin-2-one
Melting point: 285°–287° C.
1-ethyl-4,4-dimethyl-7-nitro-6-(3-thenoylamido)-4H-3,1-benzoxazin-2-one
Melting point: 277°–278° C.
1-ethyl-3,3-dimethyl-7-nitro-6-(2-pyrazinoylamido)-4H-3,1-benzoxazin-2-one
Melting point: 221° C.
4,4-dimethyl-1-isopropyl-7-nitro-6-(2-pyrazinoylamido)-4H-3,1-benzoxazin-2-one
Melting point: 253° C.
7-nitro-6-(2-pyrazinoylamido)-1,4,4-trimethyl-4H-3,1-benzoxazin-2-one
Melting point: 295°–296° C.
4,4-dimethyl-7-nitro-1-n-propyl-6-(2-pyrazinoylamido)4H-3,1-benzoxazin-2-one
Melting Point: 253° C.
1-n-butyl-4,4-dimethyl-7-nitro-6-2-pyrazinoylamido)-4H-3,1-benzoxazin-2-one
Melting point: 163°–164° C.
4,4-dimethyl-11-(2-methoxy-ethyl)-7-nitro-6-(2-pyrazinoyl-amido)-4H-3,1-benzoxazin-2-one
Melting point: 162°–163° C.

EXAMPLE G 6,7-Diamino-4,4-dimethyl-4H-3,1-benzoxazin-2-one dihydrochloride 35.6 g (0.15 mol) of 6-amino-4,4-dimethyl-7-nitro-4H-3,1-benzoxazin-2-one are dissolved in 500 ml of methanol and 60 ml of 7.5 N methanolic hydrochloric acid, 3.5 g of 10% Palladium/charcoal are added and the resulting mixture is hydrogenated for 45 minutes in an autoclave at ambient temperature under 5 bar of hydrogen pressure. The catalyst is then removed by suction filtering and the filtrate is diluted to 2 liters with ether. The precipitate is suction filtered, washed with ether and dried.

Yield: 42 g (99.9% of theory),
Melting point: 218°–220° C.

EXAMPLE 1

8,8-Dimethyl-2-(4-pyridyl)-8-hydro-(5H)-imidazo[5,4-g][3,1]benzoxazin-6-one 5.8 g (16.9 mmol) of 4,4-dimethyl-6-isonicotinoylamido-7-nitro-4H-3,1-benzoxazin-2-one are dissolved in 100 ml of glacial acetic acid, 1 g of Raney nickel is added and the mixture is hydrogenated for 1 hour at 80° C. in an autoclave under 5 bar of hydrogen pressure. The reaction product precipitated is dissolved by the addition of dimethylformamide and methanol and filtered off from the catalyst with the application of heat. The filtrate is evaporated to dryness, stirred with water, made alkaline by adding concentrated aqueous ammonia and suction filtered.

Yield: 2.2 g (44.5% of theory),
Melting point: 300° C. (from isopropanol/ethyl acetate)
$C_{16}H_{14}N_4O$ (294.31)
Calculated: C 65.30; H 4.79; N 19.04; Found: 65.03; 4.79; 18.84

EXAMPLE 2

2-(4-pyridyl)-5,8,8-trimethyl-8-hydro-(5H)-imidazo[5,4-g][3,1]benzoxazin-6-one×4 H$_2$O Prepared analogously to Example 1 from 6-isonicotinoyl-amido-7-nitro-1,4,4-trimethyl-4H-3,1-benzoxazin-2-one.
Yield: 77.6% of theory (isopropanol),
Melting point: 137°–139° C.
$C_{17}H_{16}N_2O_2 \times 4$ H$_2$O (380.40)
Calculated: C 53.96; H 5.86; N 14.81; Found: 53.75; 6.04; 14.66

EXAMPLE 3

2-(3-pyridyl)-5,8,8-trimethyl-8-hydro-(5H)-imidazo[5,4-g][3,1]benzoxazin-6-one×0.5 H$_2$O Prepared analogously to Example 1 from 6-nicotinoylamido-7-nitro-1,4,4-trimethyl-4H-3,1-benzoxazin-2-one.
Yield: 69.5% of theory,
Melting point: 285° C. (isopropanol)
$C_{17}H_{16}N_4O_2 \times 0.5$ H$_2$O (317.35)
Calculated: C 64.32; H 5.40; N 17.65; Found: 64.52; 5.46; 17.61

EXAMPLE 4

8,8-Dimethyl-2-(3-pyridyl)-8-hydro-{5H)-imidazo[5,4-g][3,1]benzoxazin-6-one

Prepared analogously to Example 1 from 4,4-dimethyl-6-nicotinoylamido-7-nitro-4H-3,1-benzoxazin-2-one.
Yield: 48.3% of theory,
Melting point: 293° C. (dioxane/water)
$C_{16}H_{14}N_4O_2$ (294.32)
Calculated: C 65.30; H 4.79; N 18.57; Found: 65.12; 4.96; 18.47

EXAMPLE 5

2-(4-Methoxy-phenyl)-5,8,8-trimethyl-8-hydro-(5H)-imidazo[5,4-g][3,1]benzoxazin-6-one Prepared analogously to Example 1 from 6-(4-methoxy-benzoylamido)-7-nitro-1,4,4-trimethyl-4H-3,1-benzoxazin-2-one.
Yield: 70.0% of theory,
Melting Point: 276°–277° C. (isopropanol/dioxane)
$C_{19}H_{19}N_3O_3$ (337.38)
Calculated: C 67.64; H 5.68; N 12.45; Found: 67.84; 5.47; 12.47

EXAMPLE 6

8,8-Dimethyl-2-(4-methoxy-phenyl)-8-hydro-(5H)-imidazo[5,4-g][3,1]benzoxazin-6-one Prepared analogously to Example 1 from 4,4-dimethyl-6-(4-methoxybenzoylamido)-7-nitro-4H-3,1-benzoxazin-2-one.
Yield: 76.9% of theory,
Melting point: 278° C. (dimethylformamide/water)
$C_{18}H_{17}N_3O_3$ (323.35)
Calculated: C 66.86; H 5.30; N 13.00; Found: 66.70; 5.47; 12.89

EXAMPLE 7

5-Ethyl-8,8-dimethyl-2-(4-pyridyl)-8-hydro-(5H)-imidazo[5,4-g][3,1]benzoxazin-6-one Prepared analogously to Example 1 from 1-ethyl-4,4-dimethyl-6-isonicotinoylamido-7-nitro-4H-3,1-benzoxazin-2-one.

Yield: 52.0% of theory,

Melting point: 281°–283° C. (ethyl acetate/isopropanol)

$C_{18}H_{18}N_4O_2$ (322.37)

Calculated: C 67.07; H 5.63; N 17.38; Found: 67.00; 5.94; 17.32

EXAMPLE 8

8,8-Dimethyl-5-(2-methoxy-ethyl)-2-(4-pyridyl)-8-hydro (5H)-imidazo[5,4-q][3.1]benzoxazin-6-one Prepared analogously to Example 1 from 4,4-dimethyl-6-isonicotinoylamido-1-(2-methoxy-ethyl)-7-nitro-4H-3,1-benzoxazin-2-one.

Yield: 57.3% of theory.

Melting point: 140° C. (ethyl acetate)

$C_{19}H_{20}N_4O_3$ (352 40)

Calculated: C 64.76; H 5.72; N 15.90; Found: 64.90; 5.78; 16.05

EXAMPLE 9

8,8-Dimethyl-2-phenyl-8-hydro-(5H)-imidazo[5,4-g][3,1]benzoxazin-6-one

Prepared analogously to Example 1 from 6-benzoylamido-4,4-dimethyl-7-nitro-4H-3,1-benzoxazin-2-one.

Yield: 33% of theory,

Melting point: 238°–239° C. (isopropanol)

$C_{17}H_{15}N_3O_2$ (293.33)

Calculated: C 69.61; H 5.15; N 14.33; Found: 69.77; 5.31; 14.13

EXAMPLE 10

8,8-Dimethyl-5-(2-methoxy-ethyl)-2-(3-pyridyl)-8-hydro-(5H-imidazo[5,4-g[3,1]benzoxazin-6-one×0.9 H₂O Prepared analogously to Example 1 from 4 4-dimethyl-1-(2-methoxyethyl)-6-nicotinoylamido-7-nitro -4H-3,1-benzoxazin-2-one.

Yield: 44% of theory,

Melting point: 111° C. (ethyl acetate/isopropanol)

$C_{19}H_{20}N_4O_3 \times 0.9$ $H_2O$ (368.61)

Calculated: C 61.91; H 5.96; N 15.20; Found: 61.99; 5.92; 15.49

EXAMPLE 11

8,8-Dimethyl-5-isopropyl-2-(4-pyridyl)-8-hydro-(5H)-imidazo[5,4-g][3,1]benzoxazin-6-one Prepared analogously to Example 1 from 4,4-dimethyl-1-isopropyl-6-isonicotinoylamido-7-nitro-H-3,1-benzoxazin-2-one.

Yield: 68% of theory,

Melting point: 165° C. (ethyl acetate)

$C_{19}H_{20}N_4O_2$ (336.40)

Calculated: C 67.84; H 5.99; N 16.66; Found: 67.60; 5.83; 16.63

EXAMPLE 12

8,8-Dimethyl-5-isopropyl-2-(3-pyridyl)-8-hydro-(5H)-imidazo[5,4-g][3,1]benzoxazin-6-one Prepared analogously to Example 1 from 4,4-dimethyl-1-isopropyl-6-isonicotinoylamido-7-nitro-4H-3,1-benzoxazin-2-one.

Yield: 35.6% of theory,

Melting point: 269°–271° C. (ethyl acetate/isopropanol)

$C_{19}H_{20}N_4O_2$ (336.40)

Calculated: C 67.84; H 6.10; N 16.64; Found: 68.05; 5.94; 16.60

EXAMPLE 13

5-Benzyl-8,8-dimethyl-2-(4-pyridyl)-8-hydro-(5H)-imidazo[5,4-g][3,1]benzoxazin-6-one Prepared analogously to Example 1 from 1-benzyl-4,4-dimethyl-6-nicotinoylamido-7-nitro-4H-3,1-benzoxazin-2-one.

Yield: 54.2% of theory,

Melting point: 227°–228° C. (ethyl acetate)

$C_{23}H_{20}N_4O_2$ (384.44)

Calculated: C 71.86; H 5.24; N 14.57; Found: 71.66; 5.34; 14.31

EXAMPLE 14

5-Benzyl-8,8-dimethyl-2-(3-pyridyl)-8-hydro-(5H)-imidazo[5,4-g][3,1]benzoxazin-6-one Prepared analogously to Example 1 from 1-benzyl-4,4-dimethyl-6-nicotinoylamido-7-nitro-4H-3,1-benzoxazin-2-one.

Yield: 36% of theory,

Melting point: 258°–259° C. (ethyl acetate)

$C_{23}H_{20}N_4O_2$ (384.44)

Calculated: C 71.86; H 5.24; N 14.57; Found: 71.83; 5.32; 14.39

EXAMPLE 15

5-Benzyl-8,8-dimethyl-2-(4-methoxy-phenyl)-8-hydro-(5H)-imidazo[5,4-g][3,1]benzoxazin-6-one Prepared analogously to Example 1 from 1-benzyl-4,4-dimethyl-6-(4-methoxy-benzoylamido)-7-nitro-4H-3,1-benzoxazin-2-one.

Yield: 57.4% of theory,

Melting point: 239°–241° C. (ethyl acetate)

$C_{25}H_{23}N_3O_3$ (413.48)

Calculated: C 72.62; 5.61; N 10.16; Found: 72.80; 5.71; 10.00

EXAMPLE 16

8,8-Dimethyl-5-n-propyl-2-(4-pyridyl)-8-hydro-(5H)imidazo[5,4-g][3,1]benzoxazin-6-one Prepared analogously to Example 1 from 4,4-dimethyl-6-isonicotinoylamido-1-n-propyl-7-nitro-4H -3,1-benzoxazin-2-one.

Yield: 76% of theory,

Melting point: 229°–231° C. (ethyl acetate)

$C_{19}H_{20}N_4O_2$ (336.40)

Calculated: C 67.84; H 5.99; N 16.66; Found: 67.76; 6.12; 16.55

EXAMPLE 17

8,8-Dimethyl-2-(4-methoxy-phenyl)-5-n-propyl-8-hydro-(5H)-imidazo]5,4-g[[3,1[benzoxazin-6-one Prepared analogously to Example 1 from 4,4-dimethyl-6-(4-methoxybenzoylamido)-7-nitro-1-n-propyl-4H-3,1-benzoxazin-2-one.

Yield: 52% of theory,

Melting point: 245°–246° C. (ethyl acetate/isopropanol)

$C_{21}H_{23}N_3O_3$ (365.43)

Calculated: C 69.02; H 6.34; N 11.50; Found: 68.90; 6.41; 11.39

EXAMPLE 18

8,8-Dimethyl-5-n-propyl-2-(3-pyridyl)-8-hydro-(5H)imidazo[5,4-g][3,1]benzoxazin-6-one Prepared analogously to Example 1 from 4,4-dimethyl-6-nicotinoylamido)-7-nitro-1-n-propyl-4H-3,1-benzoxazin-2-one.

Yield: 30% of theory,

Melting point: 199°–211° C. (ethyl acetate)

$C_{19}H_{20}N_4O_2$ (336.40)

Calculated: C 67.84; H 5.99; N 16.66; Found: 67.75; 6.12; 16.58

EXAMPLE 19

5-n-Butyl-8,8-dimethyl-2-(4-methoxy-phenyl)-8-hydro-(5H)-imidazo[5,4-g][3,1]benzoxazin-6-one Prepared analogously to Example 1 from 1-n-butyl-4,4-dimethyl-6-(4-methoxy-benzoylamido)-7-nitro-4H-3,1-benzoxazin-2-one.

Yield: 52% of theory,

Melting point: 227°–229° C. (isopropanol/ethyl acetate)

$C_{22}H_{25}N_3O_3$ (379.46)

Calculated: C 69.64; H 6.64; N 11.07; Found: 69.41; 6.72; 11.04

EXAMPLE 20

5-n-Butyl-8,8-dimethyl-2-(4-pyridyl)-8-hydro-(5H)imidazo[5,4-g][3,1]benzoxazin-6-one Prepared analogously to Example 1 from 1-n-butyl-4,4-dimethyl-6-isonicotinoylamido-7-nitro-4H-3,1-benzoxazin-2-one.

Yield: 70% of theory,

Melting point: 226°–227° C. (ethyl acetate)

$C_{20}H_{22}N_4O_2$ (350.42)

Calculated: C 68.55; H 6.33; N 15.99; Found: 68.35; 6.50; 15.70

EXAMPLE 22

5-n-Butyl-8,8-dimethyl-2-3-pyridyl)-8-hydro-(5H)imidazo[5,4-g][3,1]benzoxazin-6-one Prepared analogously to Example 1 from 1-n-butyl-4,4-dimethyl-6-nicotinoylamido-7-nitro-4H-3,1-benzoxazin-2-one.

Yield: 75.8% of theory,

Melting point: 220°–221° C. (ethyl acetate)

$C_{20}H_{22}N_4O_2$ (350.42)

Calculated: C 68.55; H 6.33; N 15.99; Found: 68.47; 6.56; 15.94

EXAMPLE 22

5-Ethyl-8,8-dimethyl-2-(4-methoxy-phenyl)-8-hydro-(5H)-imidazo[5,4-g][3,1]benzoxazin-6-one Prepared analogously to Example 1 from 1-ethyl-4,4-dimethyl-6-(4-methoxy-benzoylamido)-7-nitro-4H-3,1-benzoxazin-2-one.

Yield: 60% of theory,

Melting point: 285°–286° C. (ethyl acetate/isopropanol)

$C_{20}H_{21}N_3O_3$ (351.41)

Calculated: C 68.36; H 6.02; N 11.96; Found: 68.45; 6.09; 11.96

EXAMPLE 23

5-Ethyl-8,8-dimethyl-2-(3-pyridyl)-8-hydro-(5H)imidazo[5,4-g][3,1]benzoxazin-6-one Prepared analogously to Example 1 from 1-ethyl-4,4-dimethyl-6-nicotinoylamido-7-nitro-4H-3,1-benzoxazin-2-one.

Yield: 53% of theory,

Melting point: 274°–276° C. (ethyl acetate/isopropanol)

$C_{18}H_{18}N_4O_2$ (322.37)

Calculated: C 67.07; H 5.63; N 17.38; Found: 67.00; 5.84; 17.20

EXAMPLE 24

8,8-Dimethyl-2-(3,5-di-tert.butyl-4-hydroxy-phenyl)-8-hydro-(5H)-imidazo[5,4-g][3,1]benzoxazin-6-one Prepared analogously to Example 1 from 4,4-dimethyl-6-(3,5-di-tert.butyl-4-hydroxy-benzoyl-amido)-7-nitro-4H-3,1-benzoxazin-2-one.

Yield: 31% of theory,

Melting Point: 300° C. (isopropanol)

$C_{25}H_{31}N_3O_3$ (421.54)

Calculated: C 71.23; H 7.41; N 9.97; Found: 71.34; 7.43; 9.84

EXAMPLE 25

5-Ethyl-2-(3,5-di-tert.butyl-4-hydroxy-phenyl)-8,8-dimethyl-8-hydro-(5H)-imidazo[5,4-g][3,1]benzoxazin-6-one Prepared analogously to Example 1 from 1-ethyl-4,4-dimethyl-6-(3,5-di-tert.butyl-4-hydroxy-benzoylamido)-7-nitro-4H-3,1-benzoxazin-2-one.

Yield: 56% of theory,

Melting point: 300° C. (ethyl acetate/isopropanol)

$C_{27}H_{35}N_3O_3$ (449.59)

Calculated: C 72.13; H 7.85; N 9.35; Found: 72.21; 7.97; 9.39

EXAMPLE 26

2-(3,5-Di-tert.butyl-4-hydroxy-phenyl)-5,8,8-trimethyl-8-hydro-(5H)-imidazo[5,4-g][3,1]benzoxazin-6-one Prepared analogously to Example 1 from 6-(3,5-di-tert.butyl-4-hydroxy-benozylamido)-7-nitro-1,4,4-trimethyl-4H-3,1-benzoxazin-2-one.

Yield: 63% of theory,

Melting Point: 300° C. (ethyl acetate)

$C_{26}H_{33}N_3O_3$ (435.57)

Calculated: C 71.70; H 7.64; N 9.65; Found 71.52; 7.71; 9.54

EXAMPLE 27

2-(4-pyridyl)-8-hydro-(5H)-imidazo[5,4-g][3,1]benzoxazin-6-one

Prepared analogously to Example 1 from 6-isonicotinoylamido-7-nitro-4H-3,1-benzoxazin-2-one.

Yield: 30.1% of theory,

Melting Point: 290° C. (dimethylformamide/n-butanol)

$C_{14}H_{10}N_4O_2$ (226.26)

Calculated: C 63.15; H 3.79; N 21.04; Found: 63.20; 3.99; 21.16

EXAMPLE 28

2-phenyl-8-hydro-(5H)-imidazo[5,4-g][3,1]benzoxazin-6-one hydrochloride

Prepared analogously to Example 1 from 6-benzoylamido-7-nitro-4H-3,1-benzoxazin-2-one.

Yield: 11% of theory,

Melting Point: 300° C. (ethanol/water)

$C_{15}H_{12}N_3O_2$ (301.73)

Calculated: C 59.71; H 4.01; N 13.93; Cl 11.75; Found: 59.79; 4.29; 13.93; 11.50

EXAMPLE 29

2-Methyl-8-hydro-(5H)-imidazo[5,4-g][3,1]benzoxazin-6-one hydrochloride

Prepared analogously to Example 1 from 6-acetamido-7-nitro-4H-3,1-benzoxazin-2-one.

Yield: 12.5% of theory,

Melting Point: 305° C. (n-butanol/water)

$C_{10}N_{10}ClN_3O_2$ (239.67)

Calculated: C 50.12; H 4.21; N 17.53; Cl 14.79; Found: 49.96; 4.30; 17.64; 14.75

EXAMPLE 30

5-Methyl-2-(4-pyridyl)-8-hydro-(5H)-imidazo[5,4-g][3,1]benzoxazin-6-one×H₂O

Prepared analogously to Example 1 from 6-isonicotinoylamido-1-methyl-7-nitro-4H-3,1-benzoxazin-2-one.

Yield: 44% of theory,

Melting point: 290° C. (decomp., dioxane)

$C_{15}H_{12}N_4O_2 \times H_2O$ (298.30)

Calculated: C 60.40; H 4.73; N 18.78; Found: 60.10; 4.69; 18.70

EXAMPLE 31

5-Methyl-2-(3-pyridyl)-8-hydro-(5H)-imidazo[5,4-g][3,1]benzoxazin-6-one×0.5 H₂O

Prepared analogously to Example 1 from 6-nicotinoylamido-1-methyl-7-nitro-4H-3,1-benzoxazin-2-one.

Yield: 26% of theory,

Melting point: 264°-266° C. (dioxane)

$C_{15}H_{12}N_4O_2 \times 0.5 H_2O$ (289.29)

Calculated: C 62.28; H 4.53; N 19.37; Found: 62.18; 4.55; 19.48

EXAMPLE 32

2-(4-Methoxy-phenyl)-5-methyl-8-hydro-(5H)-imidazo[5,4-g][3,1]benzoxazin-6-one×0.5 H₂O Prepared analogously to Example 1 from 1-methyl-6-(4-methoxybenzoylamido)-7-nitro-4H-3,1-benzoxazin-2-one.

Yield: 51% of theory,

Melting point: from 258° C. (ethyl acetate/isopropanol)

$C_{15}H_{12}N_4O_2 \times 0.5 H_2O$ (289.29)

Calculated: C 64.14; H 5.07; N 13.20; Found: 64.25; 5.08; 13.20

EXAMPLE 33

8,8-Diethyl-2-(4-methoxy-ohenyl)-8-hydro-(5H)-imidazo[5,4-g][3,1]benzoxazin-6-one×H₂O Prepared analogously to Example 1 from 4,4-diethyl-6-(4-methoxy-benzoylamido)-7-nitro-4H-3,1-benzoxazin-2-one.

Yield: 50.1% of theory,

Melting point: 186°-188° C. (ethyl acetate)

$C_{20}H_{21}N_3O_3 \times H_2O$ (369.42)

Calculated: C 65.03; H 6.28; N 11.37; Found: 65.16; 6.34; 11.32

EXAMPLE 34

8,8-Diethyl-2-(4-pyridyl)-8-hydro-(5H)-imidazo[5,4-g][3,1]benzoxazin-6-one

Prepared analogously to Example 1 from 4,4-diethyl-6-isonicotinoylamido-7-nitro-4H-3,1-benzoxazin-2-one.

Yield: 50.6% of theory, Melting point: 284° C. (decomp., ethyl acetate)

$C_{18}H_{18}N_4O_2 \times H_2O$ (322.37)

Calculated: C 67.07; H 5.6; N 17.38; Found: 66.87; 5.72; 17.20

EXAMPLE 35

8,8-Diethyl-2-(3-pyridyl)-8-hydro-(b 5H)-imidazo[5,4-g][3,1]benzoxazin-6-one

Prepared analogously to Example 1 from 4,4-diethyl-6-nicotinoylamido-7-nitro-4H-3,1-benzoxazin-2-one.

Yield: 63.6% of theory,

Melting point: from 302° C. (ethyl acetate)

$C_{18}H_{18}N_4O_2$ (322.37)

Calculated: C 67.07; H 5.63; N 17.38; Found: 66.94; 5.75; 17.24

EXAMPLE 36

8,8-Diethyl-5-methyl -2-4-pyridyl)-8-hydro-(5H)imidazo[5,4-g][3,1]benzoxazin-6-one Prepared analogously to Example 1 from 4,4-diethyl-1-methyl-6-isonicotinoylamido-7-nitro-4H-3,1-benzoxazin-2-one.

Yield: 62% of theory,

Melting point: 194°-195° C. (ethyl acetate)

$C_{19}H_{20}N_4O_2$ (336.40)

Calculated: C 67.84; H 5.99; N 16.6; Found: 67.83; 6.04; 16.80

EXAMPLE 37

8,8-Diethyl-2-(4-methoxy-phenyl)-5-methyl-8-hydro-(5H)-imidazo[5,4-g][3,1]benzoxazin-6-one Prepared analogously to Example 1 from 4,4-diethyl-6-(4-methoxy-benzoylamido)-1-methyl-7-nitro-4H-3,1-benzoxazin-2-one.

Yield: 64% of theory,

Melting point: 200°-201° C. (ethyl acetate)

$C_{21}H_{23}N_3O_3$ (365.43)

Calculated: C 69.02; H 6.34; N 11.50; Found: 69.19; 6.48; 11.60

EXAMPLE 38

8,8-Diethyl-5-methyl-2-(3-pyridyl)-8-hydro-(5H)imidazo[5,4-g][3,1]benzoxazin-6-one Prepared analogously to Example 1 from 4,4-diethyl-1-methyl-6-nicotinoylamido-7-nitro-4H-3,1-benzoxazin-2one.

Yield: 62% of theory,
Melting point: 190°–191° C. (ethyl acetate)
$C_{19}H_{20}N_4O_2$ (336 40)
Calculated: C 67.84; H 5.99; N 16.66; Found: 67.83; 5.98; 16.80

EXAMPLE 39

2-(4-pyridyl)-5,8,8-triethyl-8-hydro-(5H)-imidazo[5,4-g][3,1]benzoxazin-6-one

Prepared analogously to Example 1 from 6-isonicotinoylamido-7-nitro-1,4,4-triethyl-4H-3,1-benzoxazin-2-one.

Yield: 62% of theory,
Melting point: 231°–232° C. (ethyl acetate)
$C_{20}H_{22}N_4O_2$ (350.42)
Calculated: C 68.55; H 6.33; N 15.99; Found: 68.47; 6.43; 15.93

EXAMPLE 40

2-(3-pyridyl)-5,8,8-triethyl-8-hydro-(5H)-imidazo[5,4-g][3,1]benzoxazin-6-one

Prepared analogously to Example 1 from 6-nicotinoylamido-7-nitro-1,4,4-triethyl-4H-3,1-benzoxazin-2-one.

Yield: 61% of theory,
Melting point: 188°–189° C. (ethyl acetate)
$C_{20}H_{22}N_4O_2$ (350.42)
Calculated: C 68.55; H 6.33; N 15.99; Found: 68.35; 6.29; 15.97

EXAMPLE 41

2-(4-Methoxy-phenyl)-5,8,8-triethyl-8-hydro-(5H)imidazo[5,4-g][3,1]benzoxazin-6-one Prepared analogously to Example 1 from 6-(4-methoxy-benzoylamido)-7-nitro-1,4,4-triethyl-4H-3,1-benzoxazin-2-one.

Yield: 39% of theory,
Melting Point: 218°–219° C. (ethyl acetate)
$C_{22}H_{25}N_3O_3$ (379.46)
Calculated: C 69.64; H 6.64; N 11.07; Found: 69.49; 6.68; 11.15

EXAMPLE 42

8,8-Dimethyl-2-(1-phenyl-ethyl)-8-hydro-(5H)-imidazo[5,4-g][3,1]benzoxazin-6-one Prepared analogously to Example 1 from 4,4-dimethyl-6-(2-phenyl-propionylamido)-7-nitro-4H-3,1-benzoxazin-2-one.

Yield: 58.1% of theory,
Melting point: 280° C. (isopropanol)
$C_{19}H_{19}N_3O_2$ (321.38)
Calculated: C 71.01; H 5.96; N 13.07; Found: 70.99; 6.10; 12.97

EXAMPLE 43

2-(2,4-Dimethoxy-phenyl)-8,8-dimethyl-8-hydro-(5H)imidazo[5,4-g][3,1]benzoxazin-6-one 4.4 g (0.011 mol) of 6-(2,4-dimethoxy-benzoylamido)-4,4-dimethyl-7-nitro-4H-3,1-benzoxazin-2-one are dissolved in 100 ml of glacial acetic acid, 1 g of 10% palladium/charcoal are added and the mixture is hydrogenated in an autoclave for 15 minutes at 70° C. under 5 bar of hydrogen pressure. The catalyst is removed by suction filtering, the filtrate is heated for a further 2 hours over a steam bath and the solvent is distilled off under reduced pressure. The residue is recrystallized from iso propanol/methanol.

Yield: 0.65 g (16.7% of theory),
Melting point: 285° C. (decomp.)
$C_{19}H_{19}N_3O_4$ (353.38)
Calculated: C 64.58; H 5.42; N 11.89; Found: 64.43; 5.24; 11.86

EXAMPLE 44

2-Benzyl-8,8-dimethyl-8-hydro-(5H)-imidazo[5,4-g][3,1]benzoxazin-6-one

Prepared analogously to Example 43 from 4,4-dimethyl-7-nitro-6-phenylacetamido-4H-3,1-benzoxazin-2-one.

Yield: 25.3% of theory,
Melting point: 268°–270° C. ((ethyl acetate/isopropanol)
$C_{18}H_{17}N_3O_2$ (307.35)
Calculated: C 70.34; H 5.57; N 13.67; Found: 70.23; 5.71; 13.51

EXAMPLE 45

8,8-Dimethyl-2-n-propyl-8-hydro-(5H)-imidazo[5,4-g][3,1]benzoxazin-6-one

Prepared analogously to Example 43 from 6-butyrylamido-4,4-dimethyl-7-nitro-4H-3,1-benzoxazin-2-one.

Yield: 29% of theory,
Melting point: 130°–132° C. (ethyl acetate/isopropanol)
$C_{14}H_{17}N_3O_2$ (259.31)
Calculated: C 64.85; H 6.61; N 16.20; Found: 64.74; 6.81; 1.10

EXAMPLE 46

8,8-Dimethyl-2-(1-methyl-butyl)-8-hydro-(5H)-imidazo[5,4-g][3,1]benzoxazin-6-one Prepared analogously to Example 43 from 4,4-dimethyl-6-(2-methylvalerylamido)-7-nitro-4H-3,1-benzoxazin-2-one.

Yield: 18.9% of theory,
Melting point: 280° C. (ethyl acetate/isopropanol)
$C_{16}H_{21}N_3O_2$ (287.36)
Calculated: C 66.88; H 7.37; N 14.62; Found: 67.01; 7.36; 14.73

EXAMPLE 47

8,8-Dimethyl-2-(4-methylsulfonyl-phenyl)-8-hydro-(5H)-imidazo[5,4-g][3,1]benzoxazin-6-one Prepared analogously to Example 43 from 4,4-dimethyl-6-(4-methylsulfonyl-benzoylamido)-7-nitro-4H-3,1-benzoxazin-2-one.

Yield: 52.7% of theory,
Melting point: 240° C. (ethyl acetate/isopropanol)
Calculated: C 58.20; H 4.61; N 11.32; S 8.64; Found: 58.15; 4.82; 11.36; 8.40

EXAMPLE 48

2-(4-Amino-3,5-dibromo-phenyl)-8,8-dimethyl-8-hydro-(5H)-imidazo[5,4-g][3,1]benzoxazin-6-one 5.05 g (0.01 mol) of 6-(4-amino-3,5-dibromo-benzoylamido)-4,4-dimethyl-7-nitro-4H-3,1-benzoxazin-2-one are dissolved in 100 ml of glacial acetic acid, 0.5 g of 5% platinum/charcoal are added and the mixture is hydrogenated for 1 hour in an autoclave at ambient temperature under 5 bar of hydrogen pressure. After the catalyst has been removed by suction filtering the filtrate is heated for a further 4 hours over a steam bath, the solvent is distilled off and the residue is taken up in methanol. By adding aqueous ammonia the mixture is made alkaline, the product is precipitated by the addition of water, then suction filtered, dried and recrystallized from isopropanol/ethyl acetate.

Melting point: 235° C.
Yield: 1.65 g (36% of theory),
$C_{17}H_{14}Br_2N_4O_2$ (466.16)
Calculated: C 43.80; H 3.03; N 12.02; Br 34.28; Found: 43.72; 3.16; 11.90; 33.99

EXAMPLE 49

5-Ethyl-2-(4-amino-3,5-dibromo-phenyl)-8,8-dimethyl-8-hydro-(5H)-imidazo[5,4-g][3,1]benzoxazin-6-one Prepared analogously to Example 48 from 1-ethyl-6-(4-amino-3,5-dibromo-benzoylamido)-4,4-dimethyl-7-nitro-4H-3,1-benzoxazin-2-one.
Yield: 48% of theory,
Melting point: 300° C. (ethyl acetate/isopropanol)
$C_{19}H_{18}Br_2N_4O_2$ (494.21)
Calculated: C 46.18; H 3.67; N 11.34; Br 32.34; Found: 46.00; 3.89; 11.09; 32.34

EXAMPLE 50

2-(4-Amino-3,5-dichloro-phenyl)-8,8-dimethyl-8-hydro-(5H)-imidazo[5,4-g][3,1]benzoxazin-6-one×0.3 $H_2O$ Prepared analogously to Example 48 from 6-(4-amino-3,5-dichlorobenzoylamido)-4,4-dimethyl-7-nitro-4H-3,1-benzoxazin-2-one.
Yield: 44% of theory,
Melting point: 229° C. (isopropanol/dioxane)
$C_{17}H_{14}Cl_2N_4O_2$ (382.63)
Calculated: C 53.36; H 3.85; N 14.64; Cl 18.53; Found: 53.23; 3.96; 14.49; 18.72

EXAMPLE 51

5-ethyl-2-(4-amino-3,5-dichloro-phenyl)-8-hydro-(5H)-imidazo[5,4-g][3,1]benzoxazin-6-one Prepared analogously to Example 48 from 1-ethyl-6-(4-amino-3,5-dichloro-benzoylamido)-4,4-dimethyl-7-nitro-4H-3,1-benzoxazin-2-one.
Yield: 60% of theory,
Melting point: 295°-297° C. (dioxane/methanol)
$C_{19}H_{18}C_{12}N_4O_2$ (405.30)
Calculated: C 56.31; H 4.4; N 13.82; Cl 17.50; Found: 56.26; 44.67; 13.61; 17.33

EXAMPLE 52

2-(4-Quinolyl)-8,8-dimethyl-8-hydro-(5H)-imidazo[5,4-g][3,1]benzoxazin-6-one

Prepared analogously to Example 48 from 6-(4-quinoline-carbonamido)-4,4-dimethyl-7-nitro-4H-3,1-benzoxazin-2-one.
Yield: 46% of theory,
Melting point: 270°-272° C. (dioxane/methanol)
$C_{20}H_{16}N_4O_2$ (344.38)
Calculated: C 69.76, H 4.68 , N 16.27 Found: 69.82; 4.70; 16.51

EXAMPLE 53

5-Ethyl-8,8-dimethyl-2-(2-thienyl)-8-hydro-(5H)imidazo[5,4-g][3,1]benzoxazin-6-one Prepared analogously to Example 48 from 1-ethyl-4,4-dimethyl-6-(2-thenoylamido)-7-nitro-4H-3,1-benzoxazin-2-one.
Yield: 49% of theory,
Melting point: 298°-299° C. (dioxane/water)
$C_{17}H_{17}N_3O_2$ (327.41)
Calculated: C 62.36; H 23; N 12.83; S 9.79; Found: 62.27; 5.10; 13.00; 9.57

EXAMPLE 54

5-Ethyl-8,8-dimethyl-2-(2-furyl)-8-hydro-(5H)-imidazo[5,4-g][3,1 benzoxazin-6-one Prepared analogously to Example 48 from 1-ethyl-4,4-dimethyl-6-(2-furoylamido)-7-nitro-4H-3,1-benzoxazin-2-one.
Yield: 33% of theory,
Melting point: 300°-302° C. (dioxane/isopropanol/water)
$C_{17}H_{17}N_3O_3$ (311.34)
Calculated: C 65.58; H 5.50; N 13.50; Found: 65.40; 5.58; 13.47

EXAMPLE 55

8,8-Dimethyl-2-(2-furyl)-8-hydro-(5H)-imidazo[5,4-g][3,1]benzoxazin-6-one

Prepared analogously to Example 48 from 4,4-dimethyl-6-(2-furoylamido)-7-nitro-4H-3,1-benzoxazin-2-one.
Yield: 32% of theory,
Melting point: 271°-272° C. (dioxane/ethyl acetate)
$C_{15}H_{13}N_3O_3$ (283.29)
Calculated: C 63.60; H 4.63; N 14.83; Found: 63.47; 4.74; 14.67

EXAMPLE 56

8,8-Dimethyl-2-(2-thienyl)-8-hydro-(5H)-imidazo[5,4-g][3,1]benzoxazin-6-one×0.3 $H_2O$ Prepared analogously to Example 48 from 4,4-dimethyl-7-nitro-6-(2-thenoylamido)-4H-3,1-benzoxazin-2-one.
Yield: 16% of theory,
Melting point: 275°-277° C. (ethyl acetate/isopropanol)
$C_{15}H_{13}N_3O_2 \times 0.3$ $H_2O$ (304.75)
Calculated: C 59.12; H 4.50; N 13.79; S 10.5; Found: 59.23; 4.63; 13.90; 10.38

EXAMPLE 57

8,8-Dimethyl-2-(2-morpholino-3-pyridyl)-8-hydro-(5H)-imidazo[5,4-g][3,1]benzoxazin-6-one Prepared analogously to Example 48 from 4,4-dimethyl-6-(2-morpholino-nicotinoylamido)-7-nitro-4H-3,1-benzoxazin-2-one.

Yield: 48% of theory,

Melting point: 284°–285° C. (ethyl acetate/isopropanol)

$C_{20}H_{21}N_5O_3$ (379.42)

Calculated: C 63.31; H 5.58; N 18.46; Found: 63.14; 5.64; 18.55

EXAMPLE 58

8,8-Dimethyl-2-(2-pyrazinyl)-8-hydro-(5H)-imidazo[5,4-g [3,1]benzoxazin-6-one

Prepared analogously to Example 48 from 4,4-dimethyl-7-nitro-6-(2-pyrazinoylamido)-4H-3,1-benzoxazin-2-one.

Yield: 17.5% of theory,

Melting point: 300° C. (isopropanol)

$C_{15}H_{13}N_5O_2$ (295.30)

Calculated: C 60.8; H 4.44; N 23 72; Found: 60.86; 4.62; 23.95

EXAMPLE 59

8,8-Dimethyl-2-(4-methylmercapto-phenyl)-8-hydro-(5H)-imidazo[5,4-g][3,1]benzoxazin-6-one $\times$ 0.4 $H_2O$ Prepared analogously to Example 48 from 4,4-dimethyl-6-(4-methyl-mercapto-benzoylamido)-7-nitro-4H-3,1-benzoxazin-2-one.

Yield: 30.3% of theory,

Melting point: 190°–192° C. (ethyl acetate)

$C_{18}H_{17}N_3O_2S \times 0.4$ $H_2O$ (346.62)

Calculated: C 62.37; H 5.18; N 12.12; S 9.55; Found: 62.25; 5.37; 11.90; 9.20

EXAMPLE 60

8,8-Dimethyl-2-[2-(4-pyridyl)-ethyl]-8-hydro-(5H)imidazo[5,4-g][3,1]benzoxazin-6-one $\times$ 0.8 $H_2O$ Prepared analogously to Example 1 from 4,4-dimethyl-7-nitro-6-[3-(4-pyridyl)-propionylamido]-4H-3,1-benzoxazin-2-one.

Yield: 59% of theory,

Melting point: 127°–128° C. (ethyl acetate/isopropanol)

$C_{18}H_{18}N_4O_2 \times 0.8$ $H_2O$ (336.78)

Calculated: C 64.20; H 5.87; N 16.64; Found: 64.27; 6.03; 16.42

EXAMPLE 61

8,8-Dimethyl-2-(4-pyridyl)-8-hydro-(5H)-imidazo[5,4-g][3,1]benzoxazin-6-one 5 g (0.05 mol) of triethylamine are added dropwise at ambient temperature to a suspension of 2.07 g (0.01 mol) of 6,7-diamino-4,4-dimethyl-4H-3,1-benzoxazin-2-one and 2.67 g (0.015 mol) of isonicotinic acid chloride hydrochloride in 100 ml of methylene chloride. After stirring for 1 hour at ambient temperature the solvent is distilled off, the residue is mixed with 50 ml of ethanol, 25 ml of concentrated hydrochloric acid and 10 ml of water and refluxed for 18 hours. The residue remaining after the solvents have been distilled off is taken up in ethanol, made alkaline with ammonia and water is slowly added thereto. The precipitate obtained is suction filtered and recrystallized from dioxane/water.

Yield: 1.2 g (40.8% of theory),

Melting point: 300° C.

EXAMPLE 62

8,8-Dimethyl-5-(2-methoxy-ethyl)-2-(2-pyrazinyl)-8-hydro-(5H)-imidazo[5,4-g][3,1]benzoxazin-6-one Prepared analogously to Example 1 from 4,4-dimethyl-1-(2-methoxy-ethyl)-7-nitro-6-(2-pyrzinoylamido)-4H-3,1-benzoxazin-2-one.

Yield: 46.6% of theory,

Melting Point: 227°–228° C. (ethyl acetate/isopropanol)° C.

$C_{18}H_{19}N_5O_3$ (353.38)

Calculated: C 61.18, H 5.42, N 19.82, Found 61.14; 5.48

EXAMPLE 63

8,8-Dimethyl-2-(4-nitro-phenyl)-8-hydro-(5H)-imidazo[5,4-g][3,1]benzoxazin-6-one Prepared analogously to Example 61 from 6,7-diamino-4,4-dimethyl-4H-3,1-benzoxazin-2-one and 4-nitro-benzoylchloride.

Yield: 22% of theory,

Melting point: >300° C. (dioxane/isopropanol)

$C_{17}H_{14}N_4O_4$ (338.32)

Calculated: C 60.35; H 4.17; N 16.56; Found: 60.10; 4.33; 16.38

EXAMPLE 64

8,8-Dimethyl-2-(4-pyridyl)-8-hydro-(5H)-imidazo[5,4-g][3,1]benzoxazin-6-one 2.07 g (0.01 mol) of 6,7-diamino-4,4-dimethyl-4H-3,1-benzoxazin-2-one are dissolved in 40 ml of ethanol and 2 ml of glacial acetic acid and 1.07 g (0.01 mol) of pyridine-4-aldehyde are added. The mixture is refluxed for 1 hour and then for a further 2 hours with the introduction of air. The solvent is then distilled off, the residue is suspended in ethanol, made alkaline with ammonia and water is slowly added. The precipitate obtained is suction filtered and recrystallized from dioxane/water.

Yield: 1.8 g (61.2% of theory),

Melting point: 300° C.

EXAMPLE 65

8,8-Dimethyl-2-(4-methylsulfinyl-phenyl)-8-hydro-(5H)-imidazo[5,4-g][3,1]benzoxazin-6-one $\times$ 0.5 $H_2O$ 0.69 g (0.002 mol) of 8,8-dimethyl-2-(4-methylmercapto-phenyl)-8-hydro-(5H)imidazo[5,4-g][3,1]benzoxazin-6-one are dissolved in 40 ml of glacial acetic acid, 0.2 ml of 30% hydrogen peroxide are added and the mixture is left to stand for 16 hours at ambient temperature. The residue remaining after the solvent has been eliminated is recrystallized from isopropanol/diisopropyl ether.

Yield: 0.42 g (58% of theory),

Melting point: 212°–214° C.

$C_{18}H_{17}N_3O_3S \times 0.5$ $H_2O$ (364.42)

Calculated: C 59.32; H 4.98; N 11.53; S 8.80; Found: 59.13; 5.14; 11.60; 9.01

EXAMPLE 66

2-(2-phenyl-ethyl)-5,8,8-trimethyl-8-hydro-(5H)imidazo[5,4-g][3,1]benzoxazin-6-one 0.66 g (0.002 mol) of 2-(2-phenyl-vinyl)-5,8,8,-trimethyl-8-hydro-(5H)-imidazo[5,4-g][3,1]benzoxazin-6-one are dissolved in 20 ml of methanol, 0.1 g of 10% palladium/charcoal is added and the resulting mixture is hydrogenated for 1 hour in an autoclave at ambient temperature under 5 bar of hydrogen pressure. After the catalyst has been filtered off the solvent is distilled off, the residue is stirred into water, suction filtered, dried and recrystallized from ethyl acetate.

Yield: 0.5 g (74.3% of theory),
Melting Point: 194°–195° C.
$C_{20}H_{21}N_3O_2 \times 0.25\ H_2O$ (339.91)
Calculated: C 70.67; H 6.38; N 12.36; Found: 70.70; 6.32; 12.32

EXAMPLE 67

2-(4-Hydroxy-phenyl -5,8,8-trimethyl-8-hydro-(5H)imidazo[5,4-g][3,1]benzoxazin-6-one 4.75 g (0.014 mol) of 2-(4-methoxy-phenyl)-5,8,8-trimethyl-8-hydro-(5H)imidazo[5,4-g][3,1]benzoxazin-6-one are dissolved in 250 ml of ethylene chloride, 12.5 g of boron tribromide are added at −30° C. and the mixture is stirred for 10 days at ambient temperature. After the careful addition of 50 ml of ethanol/water (1:1) the solvents are distilled off, the residue is stirred into water, suction filtered and recrystallized twice from dimethylformamide/water.

Yield: 1.1 g (22.2% of theory),
Melting point: from 270° C. (decomp.)
$C_{18}H_{17}N_3O_3 \times 1.6\ H_2O$ (352.18)
Calculated: C 61.39; H 5.78; N 11.93; Found: 61.15; 5.62; 11.73

EXAMPLE 68

2-(2-phenyl-vinyl)-5,8,8-trimethyl-8-hydro-(5H)-imidazo-[5,4-g][3,1]benzoxazin-6-one 2.15 g (0.0061 mol) of 7-amino-6-cinnamoylamido-1,4,4-trimethyl-4H-3,1 benzoxazin-2-one (prepared from 6-cinnamoylamido-7-nitro-1,4,4-trimethyl-4H-3,1-benzoxazin-2-one and iron/ concentrated hydrochloric acid in isopropanol) are dissolved in 20 ml of glacial acetic acid, heated over a steam bath for 4 hours and the solvent is distilled off. The residue is dissolved in methanol/water and made alkaline by the addition of ammonia. The precipitate obtained when more water is added is suction filtered, dried and recrystallized from ethyl acetate/isopropanol.

Yield: 1.2 g 58.8% of theory),
Melting point: 249°–250° C.
$C_{20}H_{19}N_3O_2$ (333.39)
Calculated: C 72.05; H 5.74; N 12.60; Found: 72.14; 6.01; 12.44

EXAMPLE 69

8,8-Dimethyl-5-isopropyl-2-(4-methoxy-phenyl)-8-hydro-(5H)-imidazo[5,4-g][3,1]benzoxazin-6-one $\times 3\ H_2O$ Prepared analogously to Example 68 from 7-amino-4,4-dimethyl-1-isopropyl-6-(4-methoxy-benzoylamido)-4H-3,1-benzoxazin-2-one and glacial acetic acid/hydrochloric acid.

Yield: 81.1% of theory,
Melting point: 291°–293° C. (glacial acetic acid/water=1:1)
$C_{21}H_{23}N_3O_3 \times 3\ H_2O$ (419.48)
Calculated: C 60.13; H 6.97; N 10.0; Found: 60.08; 6.78; 10.10

EXAMPLE 70

2-(4-Cyano-phenyl)-8,8-dimethyl-8-hydro-(5H)imidazo[5,4-g][3,1]benzoxazin-6-one

Prepared analogously to Example 68 from 7-amino-6-(4-cyano-benzoylamido)-4,4-dimethyl-4H-3,1-benzoxazin-2-one and glacial acetic acid.

Yield: 16 % of theory,
Melting point: 225° C. (ethyl acetate/isopropanol)
$C_{18}H_{14}N_4O_2 \times 0.6\ H_2O$ (329.14)
Calculated: C 65.69; H 4.65; N 17.02; Found: 65.78; 4.81; 16.88

EXAMPLE 71

2-(4-Piperidinyl)-5,8,8-trimethyl-8-hydro-(5H)imidazo[5,4-g][3,1]benzoxazin-6-one $\times 1.5\ H_2O$ 1.5 g (0.004 mol) of 2-(4-pyridyl)-5,8,8-trimethyl-8-hydro-(5H)-imidazo [5,4-g][3,1]benzoxazin-6-one tetrahydrate are dissolved in 150 ml of glacial acetic acid, 0.3 g of platinum oxide are added and the resulting mixture is hydrogenated for 3 hours in an autoclave at ambient temperature under 3 bars hydrogen pressure. After the catalyst has been filtered off the solvent is distilled off, saturated potassium carbonate solution is added and the mixture is extracted several times with ethyl acetate. The ethyl acetate phase is washed with saturated saline solution, dried and concentrated down to about a quarter of the original volume. When ether is added a precipitate is formed which is suction filtered and dried.

Yield: 0.65 g (48% of theory),
Melting point: 235° C. (ethyl acetate/ether)
$C_{17}H_{22}N_4O_2 \times 1.5\ H_2O$ (341.41)
Calculated: C 59.81; H 7.38; N 16.41; Found: 59.85; 7.66; 16.14

EXAMPLE 72

8,8-Dimethyl-2-mercapto-8-hydro-(5H)-imidazo[5,4-g][3,1]benzoxazin-6-one

A mixture of 100 ml of water, 50 ml of ethanol, 50 ml of carbon disulphide, 11.2 g (0.02 mol) of potassium hydroxide and 20.7 g (0.1 mol) of 6,7-diamino-4,4-dimethyl-4H-3,1-benzoxazin-2-one is refluxed for 5 hours with stirring. After cooling, it is acidified by adding about 20 ml of glacial acetic acid, the precipitate is suction filtered and recrystallized from dimethylformamide/water.

Yield: 15.6 g (62.6% of theory),
Melting point: from 293° C. (decomp.)
$C_{11}H_{11}N_3O_2S$ (249.30)
Calculated: C 53.00; H 4.45; N 16.86; S 12.86; Found: 52.88; 4.50; 17.00; 13.00

EXAMPLE 73

8,8-Dimethyl-2-methylmercapto-8-hydro-(5H)-imidazo[5,4-g][3,1]benzoxazin-6-one 2.49 g (0.01 mol) of 8,8-dimethyl-2-mercapto-8-hydro-(5H)-imidazo[5,4-g][3,1]benzoxazin-6-one are added to a sodium ethoxide solution prepared from 0.23 g (0.01 mol) of sodium and 50 ml of absolute ethanol and the resulting mixture is stirred for 10 minutes, then 0.7 ml of methyl iodide are added and the mixture is stirred for another 20 minutes.

The crystals precipitated when water is added are suction filtered, dried and recrystallized from ethylene chloride/diisopropylether.

Yield: 2 g (76% of theory),
Melting point: 273° C.
$C_{12}H_{13}N_3O_2S$ (263.31)
Calculated: C 54.74; H 4.98; N 15.96; S 12.18; Found: 55.00; 4.89; 15.67; 11.95

EXAMPLE 74

8,8-Dimethyl-2-(3-furyl)-8-hydro-(5H)-imidazo[5,4-g][3,1]-benzoxazin-6-one

Prepared analogously to Exaqmple 1 from 4,4-dimethyl-6-(3-furoylamido)-7-nitro-4H-3,1-benzoxazin-2-one
Yield: 48% of theory
Melting Point: 295°–296° C. (ethyl acetate/isopropanol)
$C_{15}H_{13}N_3O_3$ (283.29)
Calculated: C 63.60; H 4663; N 14.83; Found: 63.46; 4.69; 14.66

EXAMPLE 75

5-Ethyl-8,8-dimethyl-2-(3-furyl)-8-hydro-(5H)-imidazo[5,4-q][3,1]benzoxazin-6-one Prepared analogously to Example 1 from 1-ethyl-4,4-dimethyl-6-(3-furoylamido)-7-nitro-4H-3,1-benzoxazin-2-one
Yield: 43% of theory
$C_{17}H_{17}N_3O_3$ (311.34)
Calculated: C 65.58; H 5.50; N 13.50; Found: 65.36; 5.57; 13.34

EXAMPLE 76

8,8-Dimethyl-2-(3-thienyl)-8-hydro-(5H)-imidazo[5,y-g][3,1]-benzoxazin-6-one

Prepared analogously to Example 1 from 4,4-dimethyl-7-nitro-6-(3-thenoyl-amido)-4H-3,1-benzoxazin-2-one
Yield: 62% of theory
Melting point: 286°–287° C. (ethyl acetate/isopropanol)
$C_{15}H_{13}N_3O_2S$ (299.36)
Calculated: C 60.18; H 4.38; N 14.04; S 10.71; Found: 60.15; 4.52; 13.82; 10.55

EXAMPLE 77

5-Ethyl-8,8-dimethyl-2-(3-thienyl)-8-hydro-(5H)-imidazo[5,4-g][3,1]benzoxazin-6-one Prepared analogously to Example 1 from 1-ethyl-4,4-dimethyl-7-nitro-6-(3-thenoylamido)-4H-3,1-benzoxazin-2-one
Yield: 50% of theory
Melting point: 298°–299° C. (ethyl acetate/isopropanol)
$C_{17}H_{17}N_3O_2S$ (327.40)
Calculated: C 62.36; H 5.23; N 12.83; S 9.79; Found: 62.17; 5.21; 12.69; 9.99

EXAMPLE 78

5-Ethyl-8,8-dimethyl-2-(2-pyrazinyl)-8-hydro-(5H)-imidazo-[5.4-g][3,1]benzoxazin-6-one Prepared analogously to Example 1 from 1-ethyl-4,4-dimethyl-7-nitro-6-(2-pyrzinoylamido)4H-3,1-benzoxazin-2-one
Yield: 42.5% of theory
Melting point: 259° C. (decomp.; ethyl acetate/diisopropyl-ether)
$C_{17}H_{17}N_5O_2$ (323.35)
Calculated: C 63.15; H 5.30; N 21.66; Found: 62.95; 5.40; 21.40

EXAMPLE 79

8,8-Dimethyl-5-isopropyl-2-(2-pyrazinyl)-8-hydro-(5H)imidazo[5,4-g][3,1]benzoxazin-6-one×0.2 $H_2O$ Prepared analogously to Example 1 from 4,4-dimethyl-1-isopropyl-7-nitro-6-(2-pyrazinoylamido)-4H-3,1-benzoxazin-2-one
Yield: 40.2% of theory
Melting point: 298° C. (decomp., ethyl acetate/diisopropyl-ether)
$C_{18}H_{19}N_5O_2 \times 0.2\ H_2O$ (340.98)
Calculated: C 63.40; H 5.73; N 2.54; Found: 63.59; 5.73; 20.42

EXAMPLE 80

2-{2-pyrzinyl}-5,8,8-trimethyl-8-hydro-(5H)-imidazo[5,4-g][3,1]-benzoxazin-6-one Prepared analogously to Example 1 from 7-nitro-6-(2-pyrazinoylamido)=1,4,4-trimethyl-4H-3,1-benzoxazin-2-one.
Yield: 42% of theory
Melting point: 255°–256° C. (decomp., ethyl acetate/diisopropyl-ether)
$C_{16}H_{15}N_5O_2$ (309.33)
Calculated: C 62.13; H 4.89; N 22.64; Found: 61.93; 4.94; 22.70

EXAMPLE 81

8,8-Dimethyl-5-n-propyl-2-(2-pyrazinyl)-8-hydro-(5H)imidazo[5,4-g][3,1]benzoxazin-6-one Prepared analogously to Example 1 from 4,4-dimethyl-7-nitro-1-n-propyl-6-(2-pyrzinoylamido)-4H-3,1-benzoxazin-2-one.
Yield: 47.3% of theory
Melting point: 270°–271° C. (ethyl acetate/isopropanol)
$C_{18}H_{19}N_5O_2$ (337.38)
Calculated: C 64.08; H 5.68; N 20.76; Found: 63.94; 5.69; 20.51

EXAMPLE 82

5-n-Butyl-8,8-dimethyl-2-(2-pyrzinyl)-8-hydro-(5H)imidazo[5,4-g][3,1]benzoxazin-6-one Prepared analogously to Example 1 from 1-n-butyl-4,4-dimethyl-7-nitro-6-(2-pyrzinoylamido)-4H-3,1-benzoxazin-2-one.
Yield: 37.6% of theory
Melting point: 216°–217° C.
$C_{19}H_{21}N_5O_2$ (351.41)
Calculated: C 64.94; H 6.02; N 19.93; Found: 64.84; 6.11; 19.77

EXAMPLE I

Coated tablets containing 5 mg of 8,8-dimethyl-2-(4-pyridyl)-8-hydro-(5H)-imidazo[5,4-g][3,1]benzoxazin-6-one 1 tablet core contains:

| | |
|---|---|
| Active substance | 5.0 mg |
| Lactose | 25.2 mg |
| Corn starch | 18.0 mg |
| Microcrystalline cellulose | 10.0 mg |
| Polyvinylpyrrolidone | 1.0 mg |
| Magnesium stearate | 0.8 mg |
| | 60.0 mg |

Method

The active substance, lactose corn starch, cellulose and polyvinylpyrrolidone are mixed together and granulated with water. The granules are dried at a temperature of 45° C. and the specified quantity of magnesium stearate is added. Biconvex cores measuring 5 mm in diameter are made in a tablet making machine.

Coating

The cores are coated with a 15% polyvinylpyrrolidone solution and coating is continued with coating suspension to give a final weight of 80 mg.

EXAMPLE II

Tablets with a dividing notch containing 50 mg of 8,8-dimethyl-2-(4-pyridyl)-8-hydro-(5H)-imidazo[5,4-g][3,1]benzoxazin-6-one Composition
1 tablet contains:

| | |
|---|---|
| Active substance | 50.0 mg |
| Lactose | 40.0 mg |
| Corn starch | 17.0 mg |
| Polyvinylpyrrolidone | 2.0 mg |
| Magnesium stearate | 1.0 mg |
| | 110.0 mg |

Method

The active substance, lactose and starch are mixed together and evenly moistened with an aqueous solution of the polyvinylpyrrolidone. After the moist mass has been screened (2.0 mm mesh) and dried in a rack drier at 50° C. it is screened again (1.5 mm mesh) and the lubricant is added.

The mixture ready for compression is shaped into tablets with a dividing notch.

EXAMPLE III

Suppositories containing 100 mg of 8,8-dimethyl-2-(4-pyridyl)-8-hydro-(5H)-imidazo[5,4-g][3,1]benzoxazin-6-one 1 suppository contains:

| | |
|---|---|
| Active substance | 100.0 mg |
| Suppository mass (hard fat) | 1600.0 mg |
| | 1700.0 mg |

Method

The finely powdered active substance is homogeneously incorporated in the molten suppository mass which has being cooled to 40° C. It is then cooled to 37° C. and poured into slightly chilled moulds. Weight of suppository: 1.7 g.

EXAMPLE IV

Ampoules containing 10 mg of 8,8-dimethyl-2-(4-pyridyl)-8-hydro-(5H)-imidazo[5,4-g][3,1]benzoxazin-6-one Composition

| | |
|---|---|
| Active substance | 10.0 mg |
| 0.1 N HCl | 0.34 ml |
| Twice-distilled water ad | 1.0 ml |

Method

The substance is dissolved in water with the addition of hydrochloric acid, filtered through a diaphragm filter under aseptic conditions and then transferred into brown 2 ml injection vials which have been cleaned and sterilized.

What is claimed is:
1. New imidazo-benzoxazinones of formula

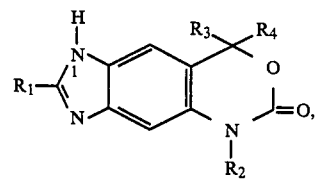

wherein

R₁ is an alkyl group optionally substituted by a phenyl or pyridyl group, an alkyl group with 4 to 6 carbon atoms, a mercapto group optionally substituted by an alkyl group, a vinylene group which is substituted in the end position by a phenyl or pyridyl group, a phenyl group optionally substituted by a halogen atom or by a hydroxy, alkoxy, mercapto, alkylmercapto, alkylsulfinyl, alkylsulfonyl, cyano, amino or nitro group, whilst a hydroxyphenyl group may additionally be substituted by one or two alkyl groups each having 1 to 4 carbon atoms or an aminophenyl group may be substituted by one or two halogen atoms; a phenyl group disubstituted by halogen atoms, hydroxy, alkoxy, mercapto, alkylmercapto, alkylsulfinyl or alkylsulfonyl groups, the substituents of the phenyl nucleus being either identical or different, a 5-or 6-membered heteroaromatic ring bound via a carbon atom, and containing an oxygen, sulphur or nitrogen atom, two or three nitrogen atoms or one nitrogen atom and one oxygen or sulphur atom, to which one or two 1,4-butadienyl groups may additionally be bonded via two adjacent carbon atoms, whilst in the case of pyridine these may additionally be substituted by an amino, alkanoylamino or morpholino group or by two halogen atoms or by one halogen atom and an amino or morpholino group, or a 5- to 7-membered saturated imino, N-alkylimino or N-alkanoyl-imino-alkylene ring, bonded via a carbon atom, in which a methylene group in the 4-position may be replaced by an imino, alkylimino or alkanoylimino group or a —CH$_2$CH$_2$— group may be replaced by an —NH—CO— group, whilst the CO group of this —NH—CO group must be linked to the existing N-atom, and moreover all the above-mentioned heteroaromatic rings and saturated rings may be substituted by an alkyl group, R$_2$ is an hydrogen atom, an alkyl group with 1 to 6 carbon atoms optionally substituted from position 2 by a hydroxy or alkoxy group, or a phenylalkyl group, R$_3$ and R$_4$, which may be identical or different, are hydrogen atoms or alkyl, whilst the alkyl moiety of all the above-mentioned groups may contain from 1 to 3 carbon atoms unless otherwise stated, the 3H-tautomers or nontoxic, pharmaceutically acceptable acid addition salts thereof.

2. The imidazo-benzoxazinones of formula I as recited in claim 1, wherein

R$_1$ is an alkyl group with 1 or 2 carbon atoms optionally substituted by a phenyl or pyridyl group; an alkyl group with 3 to 5 carbon atoms; a mercapto group optionally substituted by a methyl group; a vinylene group substituted in the end position by a phenyl or pyridyl group; a phenyl group optionally substituted by a hydroxy, methoxy, methylmercapto, methylsulfinyl, methylsulfonyl, cyano or nitro group; a dimethoxyphenyl, 3,5-di-tert.butyl-4-hydroxyphenyl, 4-amino-3,5-dihalo-phenyl, pyridyl, piperidinyl, morpholinopyridyl, quinolyl, furanyl, thienyl or pyrazinyl group, R$_2$ is a hydrogen atom, a methyl, benzyl, ethyl, n-propyl, isopropyl, 2-hydroxyethyl or 2-methoxyethyl group, R$_3$ and R$_4$, which may be identical or different, are hydrogen atoms, methyl or ethyl groups, the 3H-tautomers or nontoxic, pharmaceutically acceptable acid addition salts thereof.

3. The imidazo-benzoxazinones of formula I as recited in claim 1, wherein

R$_1$ is an alkyl group with 1 to 3 carbon atoms or a pyridyl, pyrazinyl, furyl or thienyl group, R$_2$ is a hydrogen atom or a methyl or ethyl group, R$_3$ and R$_4$ each represent a methyl group, the 3H-tautomers or nontoxic, pharmaceutically acceptable acid addition salts thereof.

4. 8,8-Dimethyl-2-(4-pyridyl)-8-hydro-(5H)-imidazo[5,4-g][3,1]benzoxazin-6-one, the 3H-tautomers or nontoxic, pharmaceutically acceptable acid addition salts thereof.

5. 5-Ethyl-8,8-dimethyl-2-(4-pyridyl)-8-hydro-(5H)-imidazo[5,4-g][3,1]benzoxazin-6-one, the 3H tautomers or nontoxic, pharmaceutically acceptable acid addition salts thereof.

6. A pharmaceutical composition of matter comprising a therapeutically effective amount of a compound as recited in claim 1 and a pharmaceutically acceptable carrier.

7. A method for treatment of chronic cardiac insufficiency in a warm-blooded animal which comprises administering to said animal a therapeutically effective amount of a compound as recited in claim 1.

8. A method for treatment of acute cardiac insufficiency in a warm-blooded animal which comprises administering to said animal a therapeutically effective amount of a compound as recited in claim 1.

9. A method for prevention of arterial thromboembolism in a warm-blooded animal which comprises administering to said animal a therapeutically effective amount of a compound as recited in claim 1.

10. A method for treatment of diseases of arterial occlusion in a warm-blooded animal which comprises administering to said animal a therapeutically effective amount of a compound as recited in claim 1.

* * * * *